US011065600B2

(12) United States Patent
Guliashvili et al.

(10) Patent No.: US 11,065,600 B2
(45) Date of Patent: Jul. 20, 2021

(54) USE OF A HEMOCOMPATIBLE POROUS POLYMER BEAD SORBENT FOR REMOVAL OF ENDOTOXEMIA-INDUCING MOLECULES

(71) Applicant: CYTOSORBENTS CORPORATION, Monmouth Junction, NJ (US)

(72) Inventors: Tamaz Guliashvili, Monmouth Junction, NJ (US); Thomas Golobish, Princeton, NJ (US); Maryann Gruda, Monmouth Junction, NJ (US); Pamela O'Sullivan, Monmouth Junction, NJ (US); Andrew Scheirer, Bethlehem, PA (US); Vincent Capponi, Monmouth Junction, NJ (US); Phillip Chan, Cherry Hill, NJ (US); Wei-Tai Young, Monmouth Junction, NJ (US)

(73) Assignee: CYTOSORBENTS CORPORATION, Monmouth Junction, NJ (US)

( * ) Notice: Subject to any disclaimer, the term of this patent is extended or adjusted under 35 U.S.C. 154(b) by 0 days.

(21) Appl. No.: 16/303,232

(22) PCT Filed: May 18, 2017

(86) PCT No.: PCT/US2017/033220
§ 371 (c)(1),
(2) Date: Nov. 20, 2018

(87) PCT Pub. No.: WO2017/205166
PCT Pub. Date: Nov. 30, 2017

(65) Prior Publication Data
US 2019/0201867 A1    Jul. 4, 2019

Related U.S. Application Data

(60) Provisional application No. 62/341,676, filed on May 26, 2016.

(51) Int. Cl.
| *A61K 31/745* | (2006.01) |
| *B01J 20/00* | (2006.01) |
| *B01J 20/26* | (2006.01) |
| *B01D 15/34* | (2006.01) |
| *B01J 20/28* | (2006.01) |
| *B01J 20/32* | (2006.01) |
| *A61K 9/00* | (2006.01) |
| *A61M 1/36* | (2006.01) |
| *B01D 15/12* | (2006.01) |

(52) U.S. Cl.
CPC .......... *B01J 20/261* (2013.01); *A61K 9/0031* (2013.01); *A61K 9/0053* (2013.01); *A61K 31/745* (2013.01); *A61M 1/3679* (2013.01); *B01D 15/34* (2013.01); *B01J 20/262* (2013.01); *B01J 20/267* (2013.01); *B01J 20/2808* (2013.01); *B01J 20/28069* (2013.01); *B01J 20/28078* (2013.01); *B01J 20/28083* (2013.01); *B01J 20/28085* (2013.01); *B01J 20/327* (2013.01); *B01J 20/3208* (2013.01); *B01J 20/3231* (2013.01); *B01J 20/3272* (2013.01); *B01J 20/3274* (2013.01); *B01J 20/3289* (2013.01); *B01D 15/125* (2013.01)

(58) Field of Classification Search
CPC ...... A61K 31/745; B01J 20/00; B01J 20/3208
USPC ........................................... 424/235.1, 236.1
See application file for complete search history.

(56) References Cited

U.S. PATENT DOCUMENTS

| 4,297,220 | A | 10/1981 | Meitzner et al. |
| 6,087,300 | A | 7/2000 | Davankov et al. |
| 2002/0197252 | A1* | 12/2002 | Brady .................. A01N 1/0247 424/140.1 |
| 2002/0198487 | A1 | 12/2002 | Brady et al. |
| 2008/0041791 | A1 | 2/2008 | Cooper et al. |
| 2013/0195792 | A1 | 8/2013 | Chan et al. |
| 2014/0158604 | A1 | 6/2014 | Chammas |
| 2014/0294751 | A1 | 10/2014 | Golobish et al. |

FOREIGN PATENT DOCUMENTS

| CN | 102247817 A | 11/2011 |
| CN | 104582751 A | 4/2015 |
| JP | 2003-320229 A | 11/2003 |
| JP | 2016-514568 A | 5/2016 |
| RU | 2439089 C1 | 1/2012 |
| RU | 2013113725 A | 10/2014 |
| WO | 2005/003152 A1 | 1/2005 |
| WO | 2015/165198 A1 | 10/2015 |
| WO | WO 2016/138528 A1 | 9/2016 |
| WO | 2017/070415 A1 | 4/2017 |

OTHER PUBLICATIONS

Bengsch et al., Extracorporeal Plasma Treatment for the Removal of Endotoxin Patients With Sepsis: Clinical Results of a Pilot Study, Shock. 2005, 23(6): 494-500.
Ginsburg, Role of Lipoteichoic Acid in Infection and Inflammation, Lancet Inft Dis. Mar. 2002, 2(3):171-179.
Harm_Falkenhagen_Hartmann, Endotoxin Adsorbents in Extracorporeal Blood Purification: Do They Fulfill Expectations? Int J Artif Organs 37.3 (2014): 222-232).
Morath et al., Structure/Function Relationships of Lipoteichoic Acids, j Endotoxin Res. 2005, 11(6):348-356.
R.L. Albright, Porous Polymers as an Anchor for Catalysis, Reactive Polymers, 4, Issue 2, (Apr. 1986), 155-174.
Sobieszcyk, et al., Combination Therapy With Polymyxin B for the Treatment of Multidrug-Resistant Gram-Negative Respiratory Tract Infections, J. Antimicrob Chemother. Aug. 5, 2004, 54(2):566-569.

(Continued)

*Primary Examiner* — Rodney P Swartz
(74) *Attorney, Agent, or Firm* — BakerHostetler

(57) ABSTRACT

The invention concerns biocompatible polymer systems comprising at least one polymer with a plurality of pores, said polymer comprising either polyol or zwitterionic groups designed to adsorb endotoxins and other inflammatory mediator molecules. The inventions are in the field of porous polymeric sorbents, also in the field of broadly reducing endotoxins in blood and blood products that can cause endotoxemia, additionally, in the field of broadly removing endotoxins by perfusion or hemoperfusion.

14 Claims, 7 Drawing Sheets

(56) References Cited

OTHER PUBLICATIONS

Tsyurupa et al., Hypercrosslinked Polystyrene: The First Nanoporous Polymeric Material, Nanotechnologies in Russia 4 (2009): 665-675.
Weinstein, et al., Neurotoxicity in Patients Treated With Intravenous Polymyxin B: Two Case Reports, Am J Health Syst Pharm, Feb. 15, 2009, 66(4): 345-347.
Yoo et al., Conformational Preferences and Antimicrobial Activities of Alkanediols, Computational and Theoretical Chemistry, 2015 vol. 1064, 15-24.
Cao et al.; "The impact of structure on elasticity, switchability, stability and functionality of an all-in-one carboxybetaine elastomer"; Biomaterials; vol. 34; Oct. 2013; p. 7592-7600 (contains English Abstract).

* cited by examiner

USE OF A HEMOCOMPATIBLE POROUS POLYMER BEAD SORBENT FOR REMOVAL OF ENDOTOXEMIA-INDUCING MOLECULES

RELATED APPLICATIONS

This application is a National Stage Application filed under 35 U.S.C. § 371 of International Application No. PCT/US2017/033220, filed May 18, 2017, which claims the benefit of U.S. Patent Application No. 62/341,676, filed May 26, 2016, the disclosures of which are incorporated herein in their entireties.

TECHNICAL FIELD

The disclosed inventions are in the field of porous polymeric sorbents. The disclosed inventions are also in the field of broadly reducing endotoxins in blood and blood products that can cause endotoxemia. Additionally, the disclosed inventions are in the field of broadly removing endotoxins by perfusion or hemoperfusion.

BACKGROUND

Gram-negative bacterial cell walls contain bound toxic substances known as endotoxins, or lipopolysaccharides (LPS). Structurally, LPS are composed of three distinct regions; O-antigen, core, and Lipid A. The O-antigen is a repetitive glycan polymer comprising the hydrophilic outermost domain of the molecule, and the composition is different for each strain of LPS. The core attaches the O-antigen to Lipid A, which is a biologically active phosphorylated glucosamine disaccharide containing multiple hydrophobic fatty acid tails. These fatty acid tails are responsible for anchoring the LPS into the bacterial cell wall. Both the core and Lipid A are highly conserved across different strains of LPS, and Lipid A is the primary toxic component.

There are two major pathways by which endotoxin can enter the bloodstream, where intravenous doses as low as 1 ng per kg body weight per hour can trigger inflammatory responses in humans. The first is through local or systemic infection by exogenous gram-negative bacteria, and the second by translocation of endogenous gram-negative bacteria, or fragments thereof, across the intestinal membrane. Once in circulation, LPS can induce an inflammatory response by binding to lipopolysaccharide binding protein (LPB) to form the LPS-LPB complex, subsequently triggering immune system and tissue cell reactions. Prolonged and upregulated inflammatory responses may lead to sepsis or systemic inflammatory response syndrome (SIRS), both of which can progress to potentially fatal septic shock and multiple organ dysfunction syndrome (MODS).

Endotoxins have also been associated with countless syndromes and diseases. These include complications from trauma, burns, and invasive surgery, and also organ-specific illnesses like liver disease, kidney dialysis complications, and autoimmune diseases.

Currently, there are a number of commercial endotoxin adsorbers. Several products are available based on Polymyxin B (PMB) immobilized on agarose gel, including Detoxi-Gel Endotoxin Removing Gel (Thermo Fisher Scientific), AffiPrep Polymyxin Matrix (BioRad), Polymyxin B agarose (Sigma-Aldrich), and Endotoxin Affisorbent (bio-WORLD). Toraymyxin (Toray Medical Co.) is a PMB-based extracorporeal device designed for selective blood purification of endotoxins via direct hemoperfusion and is approved as a therapeutic device by the health insurance system in Japan. Polymyxin B is characterized by a heptapeptide ring, a tripeptide group, and a fatty acid tail, and is an antibiotic primarily used for resistant Gram-negative infections. Positively charged diaminobutyric acid groups of PMB interact with negatively charged phosphate groups of LPS, leading to interaction between the N-terminal fatty acyl chain of PMB and lipid A fatty acyl tails, forming a very stable PMB-LPS complex. (Harm, Stephan, Dieter Falkenhagen, and Jens Hartmann. "Endotoxin Adsorbents in Extracorporeal Blood Purification: Do They Fulfill Expectations?" *Int J Artif Organs* 37.3 (2014): 222-32.).

Exploiting negatively charged groups of LI'S, anion exchange resins can also be used for LPS removal. Diethylaminoethyl-cellulose (DEAE-cellulose) resin is positively charged as a result of tertiary amine functional groups, and Bengsch et. al. have reported binding of LPS in plasmas with high affinity and capacity at physiological pH by the DEAE-cellulose adsorber. However, the reduction in endotoxin levels was accompanied by a transient, hut reversible, increase of prothrombin time. (Bengsch S, Boos K S, Nagel D, Seidel D, Inthom D. Extracorporeal plasma treatment for the removal of endotoxin in patients with sepsis: clinical results of a pilot study. *Shock.* 2005; 23(6):494-500.) The Alteco LPS adsorber (Alteco Medical AB) consists of polyethylene slabs with an immobilized special cationic peptide, HAE 27, which selectively hinds and adsorbs LI'S. Additionally, EndoTrap (Profos AG) adsorbers consist of a bacteriophage protein immobilized on Sepharose beads, where the bacteriophage protein has a high affinity for LPS molecules.

Adsorption capacities of numerous commercial endotoxin adsorbers were assessed in a study by Harm et. al. Adsorbents tested include Toraymyxin PMX-20R, Alteco LPS Adsorber, Diethylaminoethyl-sepharose (DEAE-Sepharose), Polymyxin B-Agarose, and EndoTrap red, and mobile phases used in the study include buffer solution, protein solution, serum, heparinized plasma, and whole blood. Only the Alteco LPS Adsorber and the Toraymyxin PMX-20R are hemocompatible, so only these adsorbents were tested in whole blood. These two adsorbers are also the only two of the aforementioned products that are designed for hemoperfusion applications. In batch adsorption tests using 10% adsorber in 100 ng FITC-LPS per mL solution, the adsorbing ability of DEAE-Sepharose was the best compared against other tested materials, decreasing LPS levels to $18\pm8.5\%$ of the control in 10 mM PBS buffer solution and to $37\pm4\%$ of the control in 4% (w/v) Human Serum Albumin (HSA) solution. Toraymyxin was the only other adsorber able to reduce activity below 70% and 95% in PBS and HSA solution, respectively, resulting in a reduction to $21\pm2\%$ in PBS and $87\pm6\%$ in HSA solution. Batch tests in serum and heparinized plasma were performed using 10% adsorber in 5 ng LPS per mL of spiked serum or plasma. DEAE-Sepharose was most efficient for LPS removal from serum, decreasing the value to $28\pm0.8\%$ of the control; however, it was unable to be tested in heparinized plasma due to heparin binding capabilities of DEAE-Sepharose leading to plasma clotting. PMB-Agarose was the second most efficient, reducing LPS levels to $36\pm3.6\%$ and $64\pm6.8\%$ of the control in serum and heparinized plasma, respectively. Toraymyxin was the only other adsorber able to reduce levels below 75% of the control, decreasing LAL activity to $41\pm3.5\%$ and $65\pm4.5\%$ of the control for serum and heparinized plasma, respectively. In batch tests using 5% (w/v) adsorber and LPS concentration of 3 ng/mL in whole blood, Toraymyxin reduced activity to 60±14% of the control while the Alteco LPS Adsorber was unable to reduce activity below 90% (Harm, Stephan, Dieter Falkenhagen, and Jens Hartmann. "Endotoxin Adsorbents in Extracorporeal Blood Purification: Do They Fulfill Expectations?" *Int J Artif Organs* 37.3 (2014): 222-32.).

For hemoperfusion applications, a concern with the use of immobilized PMB on a polymeric support is the potential for non-covalently bound PMB to leach from the support into the recirculating blood. Polymyxin B has been shown to induce neurotoxicity in some patients undergoing intravenous treatment (Weinstein, L, T L Doan, and M A Smith. "Neurotoxicity in patients treated with intravenous polymyxin B: Two case reports." *Am J Health Syst Pharm* 2009 Feb. 15; 66(4):345-7.). Furthermore, PMB has been shown to induce nephrotoxicity in some patients undergoing intravenous treatment (Sobieszczyk, M E, et. al. "Combination therapy with polymyxin B for the treatment of multidrug-resistant Gram-negative respiratory tract infections." *J Antimicrob Chemother.* 2004 August; 54(2):566-9). In the study by Harm et. al., referenced above, non-covalently bound PMB from Toray fibers and PMB-Agarose beads was removed through a series of washing steps and quantified using HPLC. Fibers or beads were incubated ten times in normal saline solution, followed by five times in 0.1N HCl solution. After the fifth 0.1N HCl washing step, 42±12 ng PMB/mL was found from the Toray fibers. After the fourth 0.1N HCl washing step, 27±6 ng PMB/mL was found from the PMB-Agarose beads.

As mentioned previously, endotoxins are components of the cell walls of gram-negative bacteria. Gram-negative bacteria are commonly used in the production of recombinant proteins, and many of the techniques utilized to extract the desired recombinant proteins from the bacteria cells also release lipopolysaccharides. Purification of the recombinant proteins using ion-exchange columns are not always completely successful because LPS tend to form a complex with the proteins via specific or non-specific interactions, and the entire complex becomes immobilized on the exchange column. Ropp et. al. have developed a technique using alkanediols to separate LPS from the protein-LPS complex, leaving the protein immobilized on an ion-exchange column (PCT Int. Appl. (2005), WO 2005003152 A1 20050113). Alkanediols were selected because of the reduced toxicity and flammability, compared with other reagents that accomplish similar separations.

Furthermore, alkanediols exhibit broad antimicrobial activities and have been used in cosmetics as moisturizing antimicrobial agents. In the optimized structures of dimers and trimers of 1,2-hexanediol and (<S)-3-(hexyloxy)propane-1,2-diol in water, when two hydroxyl groups become closer and the aliphatic chain becomes longer, the amphipathicity of the alkanediol is increased and thus, it is likely to penetrate more easily into membrane bilayers of the microbial cell (Yoo I K, J I I Kim, Y K Kang. "Conformational preferences and antimicrobial activities of alkanediols." *Computational and Theoretical Chemistry* 2015 vol 1064, 15-24.)

Lipoteichoic acid (LTA) is a primary component of gram-positive bacteria cell walls, and has many of the same pathogenic properties as LPS. LTA is anchored into the cell wall via a glycolipid, which plays an analogous role to lipid A in LPS (Morath S, et. al. "Structure/function relationships of lipoteichoic acids. *J Endotoxin Res.* 2005; 11(6):348-56.) If released from the cell wall, it can bind non-specifically to membrane phospholipids, or specifically to toll-like receptors, of target cells and activate the complement cascade or trigger the release of reactive species and cytokines, which may act to amplify cell damage. LTA plays an important role in infections caused by gram-positive bacteria, and in animal studies has been shown to trigger cascades resulting in multiple organ failure and septic shock in addition to meningeal inflammation, encephalomyelitis, and arthritis (Ginsburg I. "Role of lipoteichoic acid in infection and inflammation." *Lancet Infect Dis.* 2002 March; 2(3):171-9.)

SUMMARY

A novel sorbent material, described herein, offers an advantage over existing technologies in that endotoxin levels in biological fluids are decreased without the potential leaching of harmful substances, resulting in a safe and effective method. This sorbent material differs from other existing technologies due to the net neutral charge of the functional groups covalently attached to the polymeric matrix. LPS may be retained by the novel sorbent material through tortuous path, sorption, and pore capture. Several pathways can be utilized to synthesize the said resin, comprised of either a polyol group or a zwitterionic group covalently bound to a poly(styrene-co-divinylbenzene) backbone. For hemoperfusion applications, it is a requirement that the polymer is hemocompatible. Using the unactivated partial thromboplastin time (uPTT) assay as a measure of thrombogenicity, the polymers described herein exhibit minimal activation, indicating plasma-like interactions. Additionally, the sorbents are able to remove cytokines and inflammatory protein moieties simultaneously while removing endotoxins, and have the potential to exhibit antimicrobial activity. Removing either endotoxins or cytokines from an endotoxemic patient may be an insufficient treatment, as remaining endotoxin will trigger more cytokine production and remaining cytokines could still result in sepsis. By removing both the root cause of the infection and the subsequent excessive inflammatory response, this novel sorbent offers an advantage over existing technologies designed specifically for endotoxin removal.

In some aspects, the invention concerns a biocompatible polymer system comprising at least one polymer, said polymer comprising polyol or zwitterionic functionality; the polymer system capable of adsorbing endotoxins. Preferred polymers are also capable of adsorbing a broad range of toxins and inflammatory mediators having a molecular weight of from less than about 0.5 kDa to about 1,000 kDa (or about 1 kDa to about 1,000 kDa in some embodiments). Some preferred polymers are hemocompatible. Certain preferred polymer systems have geometry of a spherical bead.

Some preferred polymers are also capable of adsorbing one or more of gram-negative bacteria, gram-negative bacteria fragments, and gram-negative bacterial components. Gram-negative bacterial components include, but are not limited to, lipopolysaccharide (LPS). Other preferred polymers are also capable of adsorbing one or more of gram-positive bacteria, gram-positive bacteria fragments, and gram-positive bacterial components. Gram-positive bacterial components include, but are not limited to, lipoteichoic acid (LTA). In some embodiments, toxins and inflammatory mediators comprise one or more of cytokines, pathogen-associated molecular pattern molecules (PAMPs), damage-associated molecular pattern molecules (DAMPs), superantigens, monokines, chemokines, interferons, proteases, enzymes, peptides including bradykinin, soluble CD40 ligand, bioactive lipids, oxidized lipids, cell-free hemoglobin, cell-free myoglobin, growth factors, glycoproteins, prions, toxins, bacterial and viral toxins, drugs, vasoactive substances, foreign antigens, and antibodies.

The polymers can be made by any means known in the art to produce a suitable porous polymer. In some preferred embodiments, the polymer is made using suspension polymerization. In other embodiments, the polymer is made via emulsion polymerization, bulk polymerization, or precipitation polymerization.

The polymers are in the form of solid supports. In some preferred embodiments, the solid support is a bead. In other embodiments, the solid support is a fiber, monolithic column, or film.

Some polymer systems have a polymer pore structure that has a total volume of pore sizes in the range of from 10 Å to 40,000 Å greater than 0.1 cc/g and less than 5.0 cc/g dry polymer, while other polymer systems are nonporous. Other embodiments, have a polymer pore structure that has a total volume of pore sizes in the range of from 10 Å to 40,000 Å greater than 0.1 cc/g and less than 3.0 cc/g dry polymer, while other polymer systems are nonporous.

In certain embodiments, the polymer is in the form of hypercrosslinked or macroreticular porous polymer beads containing polyol groups. In certain other embodiments, the polymer is in the form of hypercrosslinked or macroreticular porous polymer beads containing zwitterionic groups. In preferred embodiments, the polymer is in the form of a hypercrosslinked or macroreticular porous polymer beads containing diol groups.

In certain embodiments, the polymer is in the form of nonporous polymer beads containing polyol groups. In certain other embodiments, the polymer is in the form of nonporous polymer beads containing zwitterionic groups. In preferred embodiments, the polymer is in the form of nonporous polymer beads containing diol groups.

In some embodiments, the polymer beads comprise polyol groups. The polymer beads comprising polyol groups can be produced by ring-opening reactions of premade polymer that contains epoxide groups. In preferred embodiments, the polyol groups are diol groups.

In other embodiments, the polymer beads comprising polyol groups can be produced by ester hydrolysis reactions of premade polymer that contains residual acetate groups. In preferred embodiments, the polyol groups are diol groups.

In some other embodiments, the polymer beads comprise zwitterionic functionality. The polymer beads comprising zwitterionic functionality can be produced by free-radical reactions in the presence zwitterionic monomers that contain double bonds readily available for polymerization.

Some polymer systems are constructed from polymerizable vinyl monomers containing epoxide groups which are copolymerized in the presence of cross-linker, hemocompatible monomer, monomer, and suitable porogen to yield porous polymeric polymer containing epoxide functionality. These epoxides are then converted into polyols via a ring-opening reaction in the presence of a base. In preferred systems the epoxides are converted into diols.

Still other polymer systems are constructed from polymerizable vinyl monomers containing acetate groups which are copolymerized in the presence of a cross-linker, hemocompatible monomer, monomer, and suitable porogen to yield porous polymer containing acetate groups. These acetate groups are converted into polyols via ester hydrolysis in the presence of a base. In preferred embodiments, the polyol groups are diol groups.

Some polymer systems are constructed from polymerizable vinyl monomers containing epoxide groups which are copolymerized in the presence of cross-linker, hemocompatible monomer, and monomer to yield nonporous polymeric polymer containing epoxide functionality. These epoxides are then converted into polyols via a ring-opening reaction in the presence of a base. In preferred systems the epoxides are converted into diols.

Other polymer systems are constructed from polymerizable vinyl monomers containing acetate groups which are copolymerized in the presence of cross-linker, hemocompatible monomer, and monomer to yield nonporous polymeric polymer containing acetate. These acetate groups are converted into polyols via ester hydrolysis in the presence of a base. In preferred embodiments, the polyol groups are diol groups.

Certain polymers are formed and subsequently modified to be biocompatible. Some modifications comprise forming a biocompatible surface coating or layer. Yet another aspect concerns devices for removing endotoxins from physiologic fluid comprising the biocompatible polymer system described herein. Another aspect concerns devices for also removing a broad range of protein based toxins from less than 0.5 kDa to 1,000 kDa from physiologic fluid comprising the biocompatible polymer system described herein.

Other aspects concern devices for also removing one or more of gram-negative bacteria, gram-negative bacteria fragments, and gram-negative bacterial components from physiologic fluid comprising the biocompatible polymer system described herein. Additional aspects concern devices for also removing one or more of gram-positive bacteria, gram-positive bacteria fragments, and gram-positive bacterial components from physiologic fluid comprising the biocompatible polymer system described herein.

Yet another aspect concerns devices for removing endotoxins from non-physiologic fluid comprising the biocompatible polymer system described herein. Another aspect concerns devices for also removing a broad range of protein based toxins from less than 0.5 kDa to 1,000 kDa from non-physiologic fluid comprising the biocompatible polymer system described herein.

Other aspects concern devices for also removing one or more of gram-negative bacteria, gram-negative bacteria fragments, and gram-negative bacterial components from non-physiologic fluid comprising the biocompatible polymer system described herein. Additional aspects concern devices for also removing one or more of gram-positive bacteria, gram-positive bacteria fragments, and gram-positive bacterial components from non-physiologic fluid comprising the biocompatible polymer system described herein.

Other aspects include methods of perfusion comprising passing a physiologic fluid once through or multiple times by way of a suitable extracorporeal circuit through a device comprising the biocompatible polymer system described herein.

Still other aspects concern applications wherein the polymer described herein is enterally or rectally administered.

In some aspects, the invention concerns a non-biocompatible polymer system comprising at least one polymer, said polymer comprising polyol or zwitterionic functionality; the polymer system capable of adsorbing endotoxins from physiologic fluids, laboratory or manufacturing fluids, or water systems in one or more of healthcare facilities, in-home healthcare applications, pharmaceutical facilities, biotechnology facilities, biological manufacturing processes, cell culture manufacturing processes, and laboratories. Preferred polymers are also capable of adsorbing one or more of a broad range of toxins, bacteria, bacteria fragments, and bacterial components.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF ILLUSTRATIVE EMBODIMENTS

Figure 1:
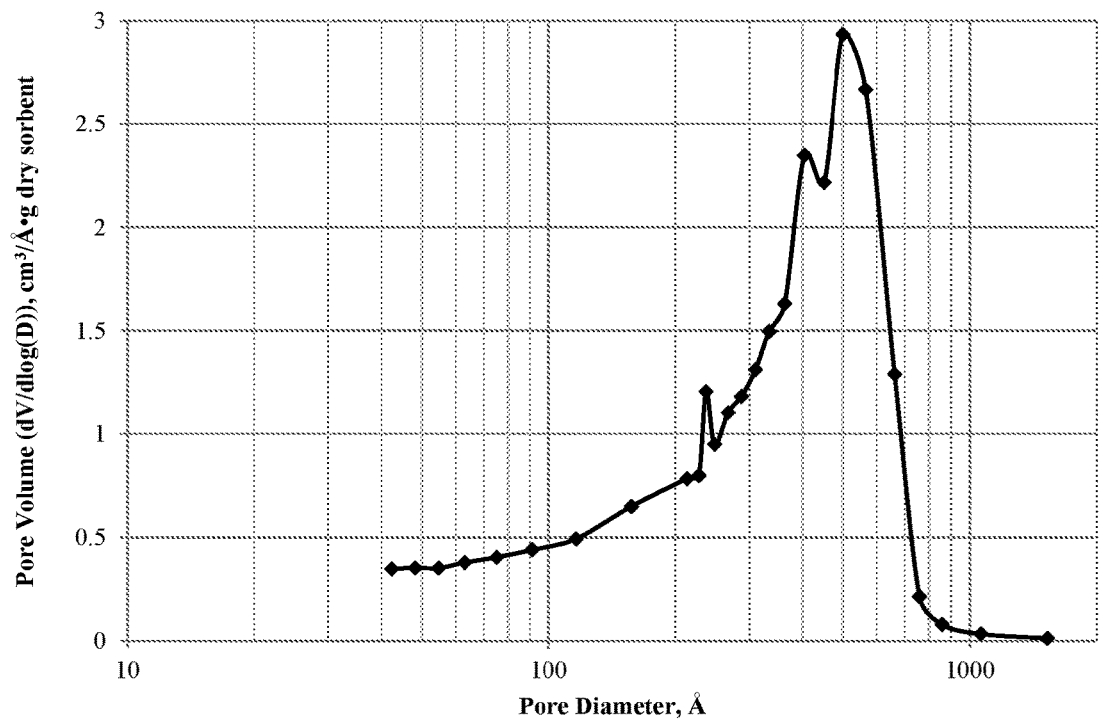
FIGS. 1, 2, 3, and 4 show log differential pore volume plots for modified polymers.

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

The present invention may be understood more readily by reference to the following detailed description taken in connection with the accompanying figures and examples, which form a part of this disclosure. It is to be understood that this invention is not limited to the specific materials, devices, methods, applications, conditions or parameters described and/or shown herein, and that the terminology used herein is for the purpose of describing particular embodiments by way of example only and is not intended to be limiting of the claimed invention. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention, which are, for clarity, described herein in the context of separate embodiments, may also be provided in combination in a single embodiment. Conversely, various features of the invention that are, for brevity, described in the context of a single embodiment, may also be provided separately or in any subcombination. Further reference to values stated in ranges includes each and every value and combination of values within that range.

The following definitions are intended to assist in understanding the present invention:

The term "biocompatible" is defined to mean the sorbent is capable of coming in contact with physiologic fluids, living tissues, or organisms, without producing unacceptable clinical changes during the time that the sorbent is in contact with the physiologic fluids, living tissues, or organisms.

The term "hemocompatible" is defined as a condition whereby a biocompatible material when placed in contact with whole blood or blood plasma results in clinically acceptable physiologic changes.

As used herein, the term "physiologic fluids" are liquids that originate from the body and can include, but are not limited to, nasopharyngeal, oral, esophageal, gastric, pancreatic, hepatic, pleural, pericardial, peritoneal, intestinal, prostatic, seminal, vaginal secretions, as well as tears, saliva, lung, or bronchial secretions, mucus, bile, blood, lymph, plasma, serum, synovial fluid, cerebrospinal fluid, urine, and interstitial, intracellular, and extracellular fluid, such as fluid that exudes from burns or wounds.

As used herein, the term "laboratory or manufacturing fluids" are defined as liquids that are used in life sciences applications that include, but are not limited to, tissue and cell culture media and additives, chemical or biologic assay media, sample preparation buffers, biologic manufacturing media, growth media, and bioreactor media.

As used herein, the term "sorbent" includes adsorbents and absorbents.

For purposes of this invention, the term "sorb" is defined as "taking up and binding by absorption and adsorption".

For the purposes of this invention, the term "perfusion" is defined as passing a physiologic fluid, once through or by way of a suitable extracorporeal circuit, through a device containing the porous polymeric adsorbent to remove toxic molecules from the fluid.

The term "hemoperfusion" is a special case of perfusion where the physiologic fluid is blood.

The term "dispersant" or "dispersing agent" is defined as a substance that imparts a stabilizing effect upon a finely divided array of immiscible liquid droplets suspended in a fluidizing medium.

The term "heparin mimicking polymer" refers to any polymer that possesses the same anticoagulant and/or anti-thrombogenic properties as heparin.

The term "macroreticular synthesis" is defined as a polymerization of monomers into polymer in the presence of an inert precipitant which forces the growing polymer molecules out of the monomer liquid at a certain molecular size dictated by the phase equilibria to give solid nanosized microgel particles of spherical or almost spherical symmetry packed together to give a bead with physical pores of an open cell structure [U.S. Pat. No. 4,297,220, Meitzner and Oline, Oct. 27, 1981; R. L. Albright, *Reactive Polymers Reactive Polymers*, 4, 155-174 (1986)].

The term "hypercrosslinked" describes a polymer in which the single repeating unit has a connectivity of more than two. Hypercrosslinked polymers are prepared by crosslinking swollen, or dissolved, polymer chains with a large number of rigid bridging spacers, rather than copolymerization of monomers. Crosslinking agents may include bis (chloromethyl) derivatives of aromatic hydrocarbons, methylal, monochlorodimethyl ether, and other bifunctional compounds that react with the polymer in the presence of Friedel-Crafts catalysts [Tsyurupa, M. P., Z. K. Blinnikova, N. A. Proskurina, A. V. Pastukhov, L. A. Pavlova, and V. A. Davankov. "Hypercrosslinked Polystyrene: The First Nanoporous Polymeric Material." *Nanotechnologies in Russia* 4 (2009): 665-75.]

Some preferred polymers comprise residues from one or more monomers, or containing monomers, or mixtures thereof, selected from acrylonitrile, allyl glycidyl ether, butyl acrylate, butyl methacrylate, cetyl acrylate, cetyl methacrylate, 3,4-dihydroxy-1-butene, dipentaerythritol diacrylate, dipentaerythritol dimethacrylate, dipentaerythritol tetraacrylate, dipentaerythritol tetramethacrylate, dipentaerythritol triacrylate, dipentaerythritol trimethacrylate, divinylbenzene, divinylformamide, divinylnaphthalene, divinylsulfone, 3,4-epoxy-1-butene, 1,2-epoxy-9-decene, 1,2-epoxy-5-hexene, ethyl acrylate, ethyl methacrylate, ethylstyrene, ethylvinylbezene, glycidyl methacrylate, methyl acrylate, methyl methacrylate, octyl acrylate, octyl methacrylate, pentaerythritol diacrylate, pentaerythritol dimethacrylate, pentaerythritol tetraacrylate, pentaerythritol tetramethacrylate, pentaerythritol triacrylate, pentaerythritol trimethacrylate, styrene, trimethylolpropane diacrylate, trimethylolpropane dimethacrylate, trimethylolpropane triacrylate, trimethylolpropane trimethacrylate, trivinylbenzene, trivinylcyclohexane, vinyl acetate, vinylbenzyl alcohol, 4-vinyl-1-cyclohexene 1,2-epoxide, vinylformamide, vinylnaphthalene, 2-vinyloxirane, and vinyltoluene.

Some embodiments of the invention use an organic solvent and/or polymeric porogen as the porogen or pore-former, and the resulting phase separation induced during polymerization yield porous polymers. Some preferred porogens are selected from, or mixtures comprised of any combination of, benzyl alcohol, cyclohexane, cyclohexanol, cyclohexanone, decane, dibutyl phthalate, di-2-ethylhexyl phthalate, di-2-ethylhexylphosphoric acid, ethylacetate, 2-ethyl-1-hexanoic acid, 2-ethyl-1-hexanol, n-heptane, n-hexane, isoamyl acetate, isoamyl alcohol, n-octane, pentanol, poly(propylene glycol), polystyrene, poly(styrene-co-methyl methacrylate), tetraline, toluene, tri-n-butylphosphate, 1,2,3-trichloropropane, 2,2,4-trimethylpentane, and xylene.

In yet another embodiment, the dispersing agent is selected from a group consisting of hydroxyethyl cellulose, hydroxypropyl cellulose, poly(diethylaminoethyl acrylate), poly(diethylaminoethyl methacrylate), poly(dimethylaminoethyl acrylate), poly(dimethylaminoethyl methacrylate), poly(hydroxyethyl acrylate), poly(hydroxyethyl methacrylate), poly(hydroxypropyl acrylate), poly(hydroxypropyl methacrylate), poly(vinyl alcohol), salts of poly(acrylic acid), salts of poly(methacrylic acid) and mixtures thereof.

Preferred sorbents are biocompatible. In another further embodiment, the polymer is biocompatible. In yet another embodiment, the polymer is hemocompatible. In still a further embodiment, the biocompatible polymer is hemocompatible. In still a further embodiment, the geometry of the polymer is a spherical bead.

In another embodiment, the biocompatible polymer comprises poly(N-vinylpyrrolidone).

In another embodiment, the biocompatible polymer comprises 1,2-diols. In another embodiment, the biocompatible polymer comprises 1,3-diols In another further embodiment, the biocompatible polymer comprises heparin mimicking polymers.

The coating/dispersant on the poly(styrene-co-divinylbenzene) resin will imbue the material with improved biocompatibility.

In still yet another embodiment, a group of cross-linkers consisting of dipentaerythritol diacrylates, dipentaerythritol dimethacrylates, dipentaerythritol tetraacrylates, dipentaerythritol tetramethacrylates, dipentaerythritol triacrylates, dipentaerythritol trimethacrylates, divinylbenzene, divinylformamide, divinylnaphthalene, divinylsulfone, pentaerythritol diacrylates, pentaerythritol dimethacrylates, pentaerythritol tetraacrylates, pentaerythritol tetramethacrylates, pentaerythritol triacrylates, pentaerythritol trimethacrylates, trimethylolpropane diacrylate, trimethylolpropane dimethacrylate, trimethylolpropane triacrylate, trimethylolpropane trimethacrylate, trivinylbenzene, trivinylcyclohexane and mixtures thereof can be used in formation of a hemocompatible hydrogel coating.

In some embodiments, the polymer is a polymer comprising at least one crosslinking agent and at least one dispersing agent. The dispersing agent may be biocompatible. The dispersing agents can be selected from chemicals, compounds or materials such as hydroxyethyl cellulose, hydroxypropyl cellulose, poly(diethylaminoethyl acrylate), poly(diethylaminoethyl methacrylate), poly(dimethylaminoethyl acrylate), poly(dimethylaminoethyl methacrylate), poly(hydroxyethyl acrylate), poly(hydroxyethyl methacrylate), poly(hydroxypropyl acrylate), poly(hydroxypropyl methacrylate), poly(vinyl alcohol), salts of poly(acrylic acid), salts of poly(methacrylic acid) and mixtures thereof; the crosslinking agent selected from a group consisting of dipentaerythritol diacrylates, dipentaerythritol dimethacrylates, dipentaerythritol tetraacrylates, dipentaerythritol tetramethacrylates, dipentaerythritol triacrylates, dipentaerythritol trimethacrylates, divinylbenzene, divinylformamide, divinylnaphthalene, divinylsulfone, pentaerythritol diacrylates, pentaerythritol dimethacrylates, pentaerythritol tetraacrylates, pentaerythritol tetramethacrylates, pentaerythritol triacrylates, pentaerythritol trimethacrylates, trimethylolpropane diacrylate, trimethylolpropane dimethacrylate, trimethylolpropane triacrylate, trimethylolpropane trimethacrylate, trivinylbenzene, trivinylcyclohexane and mixtures thereof. Preferably, the polymer is developed simultaneously with the formation of the coating, wherein the dispersing agent is chemically bound or entangled on the surface of the polymer.

In still another embodiment, the biocompatible polymer coating is selected from a group consisting of poly(diethylaminoethyl methacrylate), poly(dimethylaminoethyl methacrylate), poly(hydroxyethyl acrylate), poly(hydroxyethyl methacrylate), poly(hydroxypropyl acrylate), poly(hydroxypropyl methacrylate), poly(N-vinylpyrrolidone), poly(vinyl alcohol), salts of poly(acrylic acid), salts of poly(methacrylic acid) and mixtures thereof.

In still another embodiment, the biocompatible oligomer coating is selected from a group consisting of poly(diethylaminoethyl methacrylate), poly(dimethylaminoethyl methacrylate), poly(hydroxyethyl acrylate), poly(hydroxyethyl methacrylate), poly(hydroxypropyl acrylate), poly(hydroxypropyl methacrylate), poly(N-vinylpyrrolidone), poly(vinyl alcohol), salts of poly(acrylic acid), salts of poly(methacrylic acid) and mixtures thereof.

Some present biocompatible sorbent compositions are comprised of a plurality of pores. The biocompatible sorbents are designed to adsorb a broad range of toxins from less than 0.5 kDa to 1,000 kDa. While not intending to be bound by theory, it is believed the sorbent acts by sequestering molecules of a predetermined molecular weight within the pores. The size of a molecule that can be sorbed by the polymer will increase as the pore size of the polymer increases. Conversely, as the pore size is increased beyond the optimum pore size for adsorption of a given molecule, adsorption of said protein may or will decrease.

In certain methods, the solid form is porous. Some solid forms are characterized as having a pore structure having a total volume of pore sizes in the range of from 10 Å to 40,000 Å greater than 0.1 cc/g and less than 5.0 cc/g dry polymer.

In certain other methods, the solid form is nonporous.

In certain embodiments, the polymers can be made in bead form having a diameter in the range of 0.1 micrometers to 2 centimeters. Certain polymers are in the form of powder, beads or other regular or irregularly shaped particulates.

In some embodiments, the plurality of solid forms comprises particles having a diameter in the range for 0.1 micrometers to 2 centimeters.

In some methods, the undesirable molecules include endotoxins, gram-negative bacteria, gram-negative bacteria fragments, gram-negative bacterial components, gram-positive bacteria, gram-positive bacteria fragments, and gram-positive bacterial components, and inflammatory mediators and stimulators comprised of cytokines, pathogen-associated molecular pattern molecules (PAMPs), damage-associated molecular pattern molecules (DAMPs), superantigens, monokines, chemokines, interferons, proteases, enzymes, peptides including bradykinin, soluble CD40 ligand, bioactive lipids, oxidized lipids, cell-free hemoglobin, cell-free myoglobin, growth factors, glycoproteins, prions, toxins, bacterial and viral toxins, drugs, vasoactive substances, foreign antigens, and antibodies.

In some embodiments, sorbents include cross-linked polymeric material derived from the reaction of a cross-linker with one or more of the following polymerizable monomers, then subsequently epoxidized and ring-opened to form a polyol: acrylonitrile, allyl glycidyl ether, butyl acrylate, butyl methacrylate, cetyl acrylate, cetyl methacrylate, 3,4-dihydroxy-1-butene, dipentaerythritol diacrylate, dipentaerythritol dimethacrylate, dipentaerythritol tetraacrylate, dipentaerythritol tetramethacrylate, dipentaerythritol triacrylate, dipentaerythritol trimethacrylate, divinylbenzene, divinylformamide, divinylnaphthalene, divinylsulfone, 3,4-epoxy-1-butene, 1,2-epoxy-9-decene, 1,2-epoxy-5-hexene, ethyl acrylate, ethyl methacrylate, ethylstyrene, ethylvinylbezene, glycidyl methacrylate, methyl acrylate, methyl methacrylate, octyl acrylate, octyl methacrylate, pentaerythritol diacrylate, pentaerythritol dimethacrylate, pentaerythritol tetraacrylate, pentaerythritol tetramethacrylate, pentaerythritol triacrylate, pentaerythritol trimethacrylate, styrene, trimethylolpropane diacrylate, trimethylolpropane dimethacrylate, trimethylolpropane triacrylate, trimethylolpropane trimethacrylate, trivinylbenzene, trivinylcyclohexane, vinyl acetate, vinylbenzyl alcohol, 4-vinyl-1-cyclohexene 1,2-epoxide, vinylformamide, vinylnaphthalene, 2-vinyloxirane, and vinyltoluene. In preferred sorbents, the formed polyol is a diol.

In one other embodiment, polymeric sorbents are prepared from the reaction of a cross-linker with vinyl acetate and subsequently modified to form a bead containing polyol groups. The reaction may be a copolymerization, or a one-pot reaction in which vinyl acetate is added once initial polymerization has nearly completed, utilizing unused initiator to begin a second free-radical polymerization to add vinyl acetate groups to the surface of the polymer beads. The subsequent modification of the vinyl acetate containing polymer includes, in order: hydrolysis to convert acetate groups into hydroxyl groups, reaction with epichlorohydrin to form polymer beads containing epoxide groups, and ring-opening to convert epoxide groups into polyol groups. In preferred embodiments, polyols are diols.

Some embodiments of the invention involve direct synthesis of polymeric beads containing epoxide groups, followed by ring-opening of epoxide groups to form polyols. One or more of the following polymerizable vinyl monomer containing epoxide groups can be polymerized in the presence of cross-linker and monomer to yield polymeric beads containing above mentioned functionalities: allyl glycidyl ether, 3,4-dihydroxy-1-butene, 3,4-epoxy-1-butene, 1,2-epoxy-9-decene, 1,2-epoxy-5-hexene, glycidyl methacrylate, 4-vinyl-1-cyclohexene 1,2-epoxide, and 2-vinyloxirane. Vinyl monomers containing epoxide groups can also be copolymerized with hemocompatible monomer (NVP. 2-HEMA, etc.) to yield hemocompatible beads containing epoxide groups. In preferred embodiments, the polyols are diols.

Still other embodiments consist of hypercrosslinked polymeric sorbents containing polyol groups on the beads' surfaces. This can be accomplished via free-radical or $S_N2$ type chemistries. The chemical modification of the surface of sorbent beads, which is the case in the above modification, is facilitated by the remarkable peculiarity of the hypercrosslinked polystyrene; namely, that the reactive functional groups of the polymer are predominantly located on its surface. The hypercrosslinked polystyrene is generally prepared by crosslinking polystyrene chains with large amounts of bifunctional compounds, in particular, those bearing two reactive chloromethyl groups. The latter alkylate, in a two-step reaction, two phenyl groups of neighboring polystyrene chains according to Friedel-Crafts reaction, with evolution of two molecules of HCl and formation of a cross bridge. During the crosslinking reaction, the three-dimensional network formed acquires rigidity. This property gradually reduces the rate of the second step of the crosslinking reaction, since the reduced mobility of the second pendant functional group of the initial crosslinking reagent makes it more and more difficult to add an appropriate second partner for the alkylation reaction. This is especially characteristic of the second functional groups that happen to be exposed to the surface of the bead. Therefore, of the pendant unreacted chloromethyl groups in the final hypercrosslinked polymer, the largest portion, if not the majority of the groups, are located on the surface of the bead (or on the surface of pores). This circumstance makes it possible to predominantly modify the surface of the polymer beads by involving the above chloromethyl groups into various chemical reactions that allow attachment of biocompatible and hemocompatible monomers, and/or cross-linkers or low molecular weight oligomers. The subsequent introduction of hydroxyl groups, followed by reaction with epichlorohydrin, results in the polymer sorbent containing epoxide groups on the beads' surfaces. These epoxide groups can then be ring-opened to form polyol groups. In some preferred embodiments, the polyols are diols.

In other embodiments, hypercrosslinked polystyrene containing pendant unreacted chloromethyl groups is directly modified in the presence of one or more of the following reagents to form sorbent polymer beads containing polyols on the beads' surfaces (or on the surface of pores): (±)-3-amino-1,2-propanediol, glycerol, and other polyols. In preferred embodiments, the polyols are diols.

Still in other embodiments, the surface coating biocompatibility and hemocompatibility agent, poly(vinyl alcohol), also acts as the polyol functional group.

In some other embodiments, sorbents include cross-linked polymeric material derived from the reaction of a cross-linker with one or more of the following polymerizable monomers, then subsequently reacted with a polymerizable zwitterionic monomer in the presence of a free radical intiator: acrylonitrile, allyl glycidyl ether, butyl acrylate, butyl methacrylate, cetyl acrylate, cetyl methacrylate, 3,4-dihydroxy-1-butene, dipentaerythritol diacrylate, dipentaerythritol dimethacrylate, dipentaerythritol tetraacrylate, dipentaerythritol tetramethacrylate, dipentaerythritol triacrylate, dipentaerythritol trimethacrylate, divinylbenzene, divinylformamide, divinylnaphthalene, divinylsulfone, 3,4-epoxy-1-butene, 1,2-epoxy-9-decene, 1,2-epoxy-5-hexene, ethyl acrylate, ethyl methacrylate, ethylstyrene, ethylvinylbezene, glycidyl methacrylate, methyl acrylate, methyl methacrylate, octyl acrylate, octyl methacrylate, pentaerythritol diacrylate, pentaerythritol dimethacrylate, pentaerythritol tetraacrylate, pentaerythritol tetramethacrylate, pentaerythritol triacrylate, pentaerythritol trimethacrylate, styrene, trimethylolpropane diacrylate, trimethylolpropane dimethacrylate, trimethylolpropane triacrylate, trimethylolpropane trimethacrylate, trivinylbenzene, trivinylcyclohexane, vinyl acetate, vinylbenzyl alcohol, 4-vinyl-1-cyclohexene 1,2-epoxide, vinylformamide, vinylnaphthalene, 2-vinyloxirane, and vinyltoluene. Polymerizable zwitterionic monomers include one, or more, of the following: 2-Acrylamido-2-methyl-1-propanesulfonic acid sodium salt, [3-(Acryloylamino)propyl]-trimethylammonium chloride, 3-[[2-(Acryloyloxy)ethyl]-dimethylammonio]-propionate, [2-(Acryloyloxy)ethyl]-dimethyl-(3-sulfopropyl)-ammonium hydroxide, 2-Acryloyloxyethyl phosphorylcholine, [3-(Methacryloylamino)propyl]-trimethylammonium chloride, 3-[[2-(Methacryloyloxy)ethyl]-dimethylammonio]-propionate, [2-(Methacryloyloxy)ethyl]-dimethyl-(3-sulfopropyl)-ammonium hydroxide, and 2-Methacryloyloxyethyl phosphorylcholine.

In one embodiment, the polymers of this invention are made by suspension polymerization in a formulated aqueous phase with free radical initiation in the presence of aqueous phase dispersants that are selected to provide a biocompatible and a hemocompatible exterior surface to the formed polymer beads. In some embodiments, the beads are made porous by the macroreticular synthesis with an appropriately selected porogen (pore forming agent) and an appropriate time-temperature profile for the polymerization in order to develop the proper pore structure.

In another embodiment, polymers made by suspension polymerization can be made biocompatible and hemocompatible by further grafting of biocompatible and hemocompatible monomers or low molecular weight oligomers. It has been shown that the radical polymerization procedure does not consume all the vinyl groups of DVB introduced into copolymerization. On average, about 30% of DVB species fail to serve as crosslinking bridges and remain involved in the network by only one of two vinyl groups. The presence of a relatively high amount of pendant vinyl groups is therefore a characteristic feature of the adsorbents. It can be expected that these pendant vinyl groups are preferably exposed to the surface of the polymer beads and their macropores, if present, should be readily available to chemical modification. The chemical modification of the surface of DVB-copolymers relies on chemical reactions of the surface-exposed pendant vinyl groups and aims at converting these groups into more hydrophilic functional groups. This conversion via free radical grafting of monomers and/or cross-linkers or low molecular weight oligomers provides the initial hydrophobic adsorbing material with the property of hemocompatibility.

In yet another embodiment, the radical polymerization initiator is initially added to the dispersed organic phase, not the aqueous dispersion medium as is typical in suspension polymerization. During polymerization, many growing polymer chains with their chain-end radicals show up at the phase interface and can initiate the polymerization in the dispersion medium. Moreover, the radical initiator, like benzoyl peroxide, generates radicals relatively slowly. This initiator is only partially consumed during the formation of beads even after several hours of polymerization. This initiator easily moves toward the surface of the bead and activates the surface exposed pendant vinyl groups of the divinylbenzene moiety of the bead, thus initiating the graft polymerization of other monomers added after the reaction has proceeded for a period of time. Therefore, free-radical grafting can occur during the transformation of the monomer droplets into polymer beads thereby incorporating monomers and/or cross-linkers or low molecular weight oligomers that impart biocompatibility or hemocompatibility as a surface coating.

The hemoperfusion and perfusion devices consist of a packed bead bed of the polymer beads in a flow-through container fitted with either a retainer screen at both the exit end and the entrance end to maintain the bead bed inside the container, or with a subsequent retainer screen to collect the beads after mixing. The hemoperfusion and perfusion operations are performed by passing the whole blood, blood plasma or physiologic fluid through the packed bead bed. During the perfusion through the bead bed, the toxic molecules are retained by sorption, torturous path, and/or pore capture, while the remainder of the fluid and intact cell components pass through essentially unchanged in concentration.

In some other embodiments, an in-line filter is comprised of a packed bead bed of the polymer beads in a flow-through container, fitted with a retainer screen at both the exit end and the entrance end to maintain the bead bed inside the container. Biological fluids are passed from a storage bag once-through the packed bead bed via gravity, during which the toxic molecules are retained by sorption, torturous path, and/or pore capture, while the remainder of the fluid and intact cell components pass through essentially unchanged in concentration.

Certain polymers useful in the invention (as is or after further modification) are macroporous polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): macroporous polymeric sorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade sorbents such as Amberchrom™ CG 71,s,m,c, Amberchrom™ CG 161,s,m,c, Amberchrom™ CG 300,s,m,c, and Amberchrom™ CG 1000,s,m,c. Dow Chemical Company: Dowex™ Optipore™ L-493, Dowex™ Optipore™ V-493, Dowex™ Optipore™ V-502, Dowex™ Optipore™ L-285, Dowex™ Optipore™ L-323, and Dowex™ Optipore™ V-503. Lanxess (formerly Bayer and Sybron): Lewatit™ VPOC 1064 MD PH, Lewatit™ VPOC 1163, Lewatit™ OC EP 63, Lewatit™ S 6328 Å, Lewatit™ OC 1066, and Lewatit™ 60/150 MIBK. Mitsubishi Chemical Corporation:

Diaion™ HP 10, Diaion™ HP 20, Diaion™ HP 21, Diaion™ HP 30, Diaion™ HP 40, Diaion™ HP 50, Diaion™ SP70, Diaion™ SP 205, Diaion™ SP 206, Diaion™ SP 207, Diaion™ SP 700, Diaion™ SP 800, Diaion™ SP 825, Diaion™ SP 850, Diaion™ SP 875, Diaion™ HP 1MG, Diaion™ HP 2MG, Diaion™ CHP 55 Å, Diaion™ CHP 55Y, Diaion™ CHP 20 Å, Diaion™ CHP 20Y, Diaion™ CHP 2MGY, Diaion™ CHP 20P, Diaion™ HP 20SS, Diaion™ SP 20SS, Diaion™ SP 207SS. Purolite Company: Purosorb™ AP 250 and Purosorb™ AP 400, and Kaneka Corp. Lixelle beads.

Other certain polymers useful in the invention (as is or after further modification) are cellulosic porous materials. Such modifications could include the addition of lipophilic substrates that comprise aryl or alkyl groups, along with polyol or zwitterionic substrates, added via free-radical or $S_N2$ type chemistries.

Various proteins may be adsorbed by the composition of the instant disclosure. Some of these proteins and their molecular weights are shown in the table below.

| Protein | Molecular Weight (Da) |
| --- | --- |
| PAF (Platelet Activating Factor) | 524 |
| bilirubin | 548.6 |
| heme b | 616.5 |
| MIP-1alpha | 8,000 |
| Complement C5a | 8,200 |
| Complement C3a | 9,089 |
| IL-8 | 9,000 |
| S100B (dimerizes) | 10,000 |
| β-2 microglobulin | 11,800 |
| Procalcitonin | 13,000 |
| Phospholipase A2, secretory PLA2 type I pancreatic | 14,000 |
| PLA2G2A | 16,083 |
| IL-7 | 17,400 |
| Myoglobin | 17,699 |
| Trypsin-human pancreas | 23,300 |
| IL-6 | 23,718 |
| Toxic shock syndrome toxin 1 (TSST-1 | 24,000 |
| Enterotoxin B, S aureus | 24,500 |
| HMGB1 | 24,894 |
| Interferon gamma | 25,000 |
| Chymotrypsin | 25,000 |
| Elastase (neutrophil) | 25,000 |
| Trypsin | 26,488 |
| PF4 | 27,100 |
| Enterotoxin A, S. aureus | 27,800 |
| alpha toxin A&B, S. aureus | 28,000 |
| PCNA, proliferating cell nuclear antigen | 29,000 |
| Arginse I | 35,000 |
| Carboxypeptidase A | 35,000 |
| Thrombin | 36,700 |
| alpha-1 antitrypsin | 44,324 |
| TNF-alpha | 52,000 |
| Activated Protein C | 56,200 |
| Amylase | 57,000 |
| hemopexin | 57,000 |
| alpha-1 antichymotrypsin | 55,000-68,000 |
| Diptheria toxoid | 62,000 |
| hemoglobin, oxy | 64,000 |
| Pseudomonas Exotoxin A | 66,000 |
| ShigaToxin (A 32 kDa, 5 × B 7.7 kDa) | 69,000 |
| Calpain-1 (human erythrocytes) | 112,00 |
| C reactive Protein (5 × 25 kDa) | 115,000 |
| Myeloperoxidase (neutrophils) | 150,000 |
| Immunoglobulin G IgG | 150,000 |
| NOS synthase | 150,000 |
| Immunoglobulin A IgA | 162,000 |
| Immunoglobulin E (IgE) | 190,000 |
| Immunoglobulin M IgM | 950,000 |

The following examples are intended to be exemplary and non-limiting.

Example 1: Base Sorbent Synthesis CY14175 & CY15077

Reactor Setup: a 4-neck glass lid was affixed to a 3 L jacketed cylindrical glass reaction vessel using a stainless steel flange clamp and PFTE gasket. The lid was fitted with a PFTE stirrer bearing, RTD adapter, and water-cooled reflux condenser. A stainless steel stirring shaft having five 60° agitators was fit through the stirrer bearing and inserted into a digital overhead stirrer. An RTD was fit through the corresponding adapter, and connected to a PolyStat circulating heating and chilling unit. Compatible tubing was used to connect the inlet and outlet of the reaction vessel jacket to the appropriate ports on the PolyStat. The unused port in the lid was used for charging the reactor and was plugged at all other times.

Polymerization: Aqueous phase and organic phase compositions are shown below, in Table I and Table II, respectively. Ultrapure water was split into approximately equal parts in two separate Erlenmeyer flasks, each containing a PFTE coated magnetic stir bar. Poly(vinyl alcohol) (PVA), having a degree of hydrolysis of 85.0 to 89.0 mol percent and a viscosity of 23.0 to 27.0 cP in a 4% aqueous solution at 20° C., was dispersed into the water in the first flask and heated to 80° C. on a hot plate with agitation. Salts (see Table 1, MSP, DSP, TSP and Sodium nitrite) were dispersed into the water in the second flask and heated to 80° C. on a hot plate with agitation. Circulation of heat transfer fluid from the PolyStat through the reaction vessel jacket was started, and fluid temperature heated to 60° C. Once PVA and salts dissolved, both solutions were charged to the reactor, one at a time, using a glass funnel. The digital overhead stirrer was powered on and the rpm set to a value to form appropriate droplet sizes upon organic phase addition. Temperature of the aqueous phase in the kettle was set to 70° C. The organic phase was prepared by adding benzoyl peroxide (BPO) to the divinylbenzene (DVB) in a 2 L Erlenmeyer flask and swirling until completely dissolved. 2,2,4-trimethylpentane and toluene were added to the flask, which was swirled to mix well. Once the temperature of the aqueous phase in the reactor reached 70° C., the organic phase was charged into the reactor using a narrow-necked glass funnel. Temperature of the reaction volume dropped upon the organic addition. A temperature program for the PolyStat was started, heating the reaction volume from 60 to 77° C. over 30 minutes, 77 to 80° C. over 30 minutes, holding the temperature at 80° C. for 960 minutes, and cooling to 20° C. over 60 minutes.

TABLE I

| Aqueous Phase Composition | |
| --- | --- |
| Reagent | Mass (g) |
| Ultrapure water | 1500.000 |
| Poly(vinyl alcohol) (PVA) | 4.448 |
| Monosodium phosphate (MSP) | 4.602 |
| Disodium phosphate (DSP) | 15.339 |
| Trisodium phosphate (TSP) | 9.510 |
| Sodium nitrite | 0.046 |
| Total | 1533.899 |

TABLE II

Organic Phase Compositions

| Reagent | CY14175 Mass (g) | CY15077 Mass (g) |
|---|---|---|
| Divinylbenzene, 63% (DVB) | 508.751 | 498.383 |
| 2,2,4-trimethylpentane (Isooctane) | 384.815 | 482.745 |
| Toluene | 335.004 | 222.404 |
| Benzoyl peroxide, 98% (BPO) | 3.816 | 3.738 |
| Total (excluding BPO) | 1228.571 | 1203.532 |

Work-up: reaction volume level in the reactor was marked. Overhead stirrer agitation was stopped, residual liquid siphoned out of the reactor, and the reactor filled to the mark with ultrapure water at room temperature. Overhead stirrer agitation was restarted and the slurry heated to 70° C. as quickly as possible. After 30 minutes, agitation was stopped and residual liquid siphoned out. Polymer beads were washed five times in this manner. During the final wash, the slurry temperature was cooled to room temperature. After the final water wash, polymer beads were washed with 99% isopropyl alcohol (IPA) in the same manner. 99% IPA was siphoned out and replaced with 70% IPA before transferring the slurry into a clean 4 L glass container. Unless noted otherwise, on an as-needed basis the polymer was steam stripped in a stainless steel tube for 8 hours, rewet in 70% IPA, transferred into DI water, sieved to obtain only the portion of beads having diameters between 300 and 600 m, and dried at 100° C. until no further weight loss on drying was observed.

Cumulative pore volume data for polymers CY14175 and CY15077, measured by nitrogen desorption isotherm and mercury intrusion porosimetry, respectively, are shown below in Tables III and IV, respectively.

TABLE III

Nitrogen Desorption Isotherm Data for CY14175

| Pore Diameter Range (Å) | Pore size Diameter (Å) | Cumulative Pore Volume (cm³/g) |
|---|---|---|
| 1411.9-1126.5 | 1236.809577 | 0.018062878 |
| 1126.5-981.7 | 1043.979923 | 0.038442381 |
| 981.7-752.9 | 836.7828769 | 0.141559621 |
| 752.9-659.9 | 700.1024343 | 0.24336622 |
| 659.9-572.0 | 609.4657394 | 0.416511969 |
| 572.0-483.1 | 519.8089977 | 0.646318614 |
| 483.1-449.8 | 465.2234212 | 0.730406771 |
| 449.8-401.4 | 422.7246485 | 0.849167577 |
| 401.4-354.1 | 374.6289335 | 0.956165766 |
| 354.1-337.9 | 345.6019761 | 0.997336398 |
| 337.9-313.5 | 324.758962 | 1.0547802 |
| 313.5-290.8 | 301.2432086 | 1.09667858 |
| 290.8-262.8 | 275.299967 | 1.164042391 |
| 262.8-247.2 | 254.510376 | 1.199751164 |
| 247.2-233.6 | 240.0176376 | 1.228796957 |
| 233.6-220.1 | 226.435352 | 1.256631669 |
| 220.1-208.6 | 213.9982044 | 1.283063762 |
| 208.6-130.5 | 151.2300725 | 1.464027373 |
| 130.5-105.7 | 115.2567614 | 1.527062065 |
| 105.7-82.8 | 91.14860242 | 1.592486039 |
| 82.8-67.6 | 73.42901881 | 1.641003444 |
| 67.6-57.5 | 61.59836256 | 1.6763711 |
| 57.5-51.6 | 54.15491457 | 1.699539142 |
| 51.6-45.0 | 47.72291376 | 1.728282889 |
| 45.0-39.8 | 42.01726183 | 1.752728216 |
| 39.8-35.8 | 37.55877213 | 1.779016164 |
| 35.8-31.8 | 33.51596841 | 1.8086605 |
| 31.8-28.7 | 30.02327371 | 1.82963357 |
| 28.7-26.0 | 27.18773181 | 1.850084632 |
| 26.0-23.3 | 24.46989555 | 1.87529426 |

TABLE III-continued

Nitrogen Desorption Isotherm Data for CY14175

| Pore Diameter Range (Å) | Pore size Diameter (Å) | Cumulative Pore Volume (cm³/g) |
|---|---|---|
| 23.3-20.9 | 21.92055755 | 1.902736527 |
| 20.9-18.5 | 19.52461159 | 1.935789448 |
| 18.5-16.2 | 17.16324429 | 1.97779901 |

TABLE IV

Mercury Intrusion Data for CY15077

| Pore size Diameter (Å) | Cumulative Intrusion (mL/g) |
|---|---|
| 226299.0625 | 3.40136E-30 |
| 213166.0781 | 0.001678752 |
| 201295.1563 | 0.002518128 |
| 172635.8125 | 0.004364755 |
| 139538.0625 | 0.007554384 |
| 113120.7813 | 0.011919139 |
| 90542.36719 | 0.01645177 |
| 78733.25781 | 0.0203129 |
| 72446.375 | 0.022327403 |
| 60340.40234 | 0.027867284 |
| 48343.83984 | 0.035327822 |
| 39009.13672 | 0.040918175 |
| 32136.4082 | 0.04899035 |
| 25330.65625 | 0.063195683 |
| 20981.51563 | 0.079529688 |
| 16219.86426 | 0.108860672 |
| 13252.41211 | 0.141730919 |
| 10501.53613 | 0.193969816 |
| 8359.911133 | 0.262399256 |
| 6786.30127 | 0.345866203 |
| 5538.122559 | 0.438174427 |
| 4337.931152 | 0.563276172 |
| 3501.674805 | 0.681870878 |
| 2838.742188 | 0.804727197 |
| 2593.016846 | 0.865813017 |
| 2266.688965 | 0.938610673 |
| 1831.041748 | 1.056586146 |
| 1509.850708 | 1.163395643 |
| 1394.006104 | 1.21002543 |
| 1294.780151 | 1.257248282 |
| 1207.692627 | 1.293158531 |
| 1131.860962 | 1.326992273 |
| 1065.099976 | 1.35812819 |
| 953.1816406 | 1.405935764 |
| 884.0358887 | 1.445426106 |
| 823.5491333 | 1.478719592 |
| 770.9108276 | 1.510579824 |
| 722.4724731 | 1.537048101 |
| 684.6119995 | 1.564400196 |
| 672.187561 | 1.581117511 |
| 636.7885742 | 1.60271585 |
| 604.7248535 | 1.621845484 |
| 558.1287231 | 1.651492 |
| 518.2624512 | 1.678913713 |
| 483.5536499 | 1.708594561 |
| 453.5110779 | 1.735918999 |
| 426.9998474 | 1.755934 |
| 403.1251526 | 1.783603072 |
| 382.7776794 | 1.793849826 |
| 362.7162476 | 1.817784309 |
| 342.3734436 | 1.838774562 |
| 330.1105042 | 1.851493955 |
| 315.5238037 | 1.869742155 |
| 302.2973938 | 1.885128617 |
| 290.2946777 | 1.895119786 |
| 279.1246643 | 1.912378907 |
| 268.7442627 | 1.924305081 |
| 259.1106873 | 1.936048627 |
| 241.8737793 | 1.955100656 |
| 226.7678223 | 1.972970247 |
| 213.3626251 | 1.988123298 |

TABLE IV-continued

Mercury Intrusion Data for CY15077

| Pore size Diameter (Å) | Cumulative Intrusion (mL/g) |
|---|---|
| 201.4908142 | 2.007521152 |
| 194.9888611 | 2.022114754 |
| 188.9506989 | 2.033871174 |
| 180.582901 | 2.035052776 |
| 172.8530121 | 2.050720692 |
| 164.9621735 | 2.062945843 |
| 157.8110657 | 2.071056128 |
| 151.1540375 | 2.082133055 |
| 143.9185333 | 2.096480608 |
| 138.4670563 | 2.106938839 |
| 132.8492737 | 2.119287968 |
| 129.5760345 | 2.126605988 |
| 126.5438614 | 2.126605988 |
| 124.2635574 | 2.132267475 |
| 120.8976135 | 2.141504765 |
| 117.3792267 | 2.150759459 |
| 114.791893 | 2.154810667 |
| 111.9475937 | 2.162935257 |
| 108.8830032 | 2.167646885 |
| 106.6480179 | 2.174062729 |
| 104.5217743 | 2.179908991 |
| 102.4295197 | 2.179908991 |
| 100.1580353 | 2.182951927 |
| 98.29322052 | 2.184018135 |
| 96.44822693 | 2.191127539 |
| 94.42159271 | 2.198545218 |
| 91.52587891 | 2.209161043 |
| 89.25807953 | 2.209312439 |
| 87.0777359 | 2.215425491 |
| 85.42358398 | 2.221472025 |
| 83.62612915 | 2.232139587 |
| 82.11174011 | 2.237514496 |
| 79.91614532 | 2.239231586 |
| 78.01462555 | 2.239560127 |
| 76.19993591 | 2.239560127 |
| 75.09249115 | 2.239560127 |
| 73.41201019 | 2.239560127 |
| 72.23709869 | 2.240245819 |
| 71.09960175 | 2.242422104 |
| 69.86301422 | 2.243849993 |
| 68.40761566 | 2.257676363 |
| 67.13697815 | 2.259181261 |
| 66.03359222 | 2.266284466 |
| 65.08189392 | 2.270181179 |
| 64.04368591 | 2.272682428 |
| 62.38490295 | 2.280714512 |
| 61.32764053 | 2.280714512 |
| 60.30379868 | 2.287917852 |
| 59.41370392 | 2.287917852 |
| 58.54679489 | 2.293802738 |
| 57.79866409 | 2.297607183 |
| 56.88977814 | 2.299046278 |
| 55.9213295 | 2.302111387 |
| 54.98665237 | 2.303381443 |

Example 2: Polymer Modification CY15129

Epoxidation: 50.8 g dried base polymer CY14175 was added to a 1 L jacketed glass reactor, which was equipped with a Teflon coated agitator and RTD probe. 300 mL acetic anhydride (99%) was added to the reactor containing dried base polymer. The mixture was cooled to 5° C. with constant agitation at 100 RPM. 30 mL hydrogen peroxide solution (30% in water) was added over a 30 minute period. Reaction temperature was maintained between 10 and 15° C. for 24 hours with agitation at 100 RPM.

Work-up: reaction mixture was washed with acetic acid, and then with DI water until the pH of the reaction supernatant was neutral. Polymer was then dried at 80° C. until no further loss on drying was observed. Dry polymer yield was 61.6 g.

The epoxidation procedure described above should never be scaled to reaction volumes greater than 1 L. Formation of diacetyl peroxide can occur if peracetic acid, the desired intermediate compound, combines with excess acetic anhydride. Diacetyl peroxide is known to be a shock-sensitive explosive. It is therefore emphasized that an alternative epoxidation procedure be used whenever possible.

Ring opening: 20.0 g dried epoxide functionalized polymer was added to a 500 mL jacketed glass reactor, which was equipped with a Teflon coated agitator and RTD probe. 70 mL 70% isopropanol (IPA) was charged to the reactor and the mixture was agitated at 100 RPM. 70 mL 1M NaOH$_{(aq)}$ was added slowly. Reaction temperature was increased to 70° C. and held at 70° C. for 24 hours with agitation at 100 RPM.

Work-up: reaction was cooled to room temperature and washed with DI water until the pH of reaction supernatant was neutral. The result of the procedure was a poly(styrene-co-divinylbenzene) resin functionalized with 1,2-diol groups.

Cumulative pore volume data for polymer CY15129, measured by nitrogen desorption isotherm, is shown below in Table V. Table VI displays atomic concentrations for polymer CY15129, as measured by XPS. A log differential pore volume plot for polymer CY15129 is presented in FIG. 1, below.

Thrombogenicity was measured by the uPTT assay in which materials were compared to the negative control (plasma alone), positive control (glass beads) and reference beads to determine the degree of contact activation activity. In the uPTT assay, the % change in clot formation over time as compared to the reference materials was determined, then grouped according to: <25% activators, 25-49% moderate activators, 50-74% mild activators, 75-100% minimal and >100% non-activators of the intrinsic coagulation pathway. Polymer CY15129, 97%, was a minimal activator.

TABLE V

Nitrogen Desorption Isotherm Data for CY15129

| Pore Diameter Range (Å) | Average Diameter (Å) | Cumulative Pore Volume (cm³/g) |
|---|---|---|
| 2034.9-1317.1 | 1526.474454 | 0.002514444 |
| 1317.1-935.6 | 1062.084035 | 0.007514721 |
| 935.6-803.2 | 859.0838936 | 0.012804653 |
| 803.2-724.3 | 759.5729583 | 0.022385884 |
| 724.3-618.7 | 663.0038051 | 0.11069146 |
| 618.7-528.4 | 566.229207 | 0.293450368 |
| 528.4-477.4 | 500.2010743 | 0.422802223 |
| 477.4-427.8 | 449.747968 | 0.528381351 |
| 427.8-385.3 | 404.2054307 | 0.635018474 |
| 385.3-345.0 | 362.8353743 | 0.713148267 |
| 345.0-323.2 | 333.3669226 | 0.755679912 |
| 323.2-298.1 | 309.5707625 | 0.801803022 |
| 298.1-277.2 | 286.8210159 | 0.83919397 |
| 277.2-257.8 | 266.7224264 | 0.873960046 |
| 257.8-239.1 | 247.7159777 | 0.904840173 |
| 239.1-233.9 | 236.4822841 | 0.916370883 |
| 233.9-221.5 | 227.3553143 | 0.935307969 |
| 221.5-206.1 | 213.192271 | 0.959816922 |
| 206.1-137.2 | 157.3515944 | 1.074317205 |
| 137.2-104.8 | 116.2916904 | 1.132011868 |
| 104.8-83.2 | 91.22080984 | 1.176129172 |
| 83.2-69.8 | 75.13316152 | 1.206969053 |
| 69.8-58.7 | 63.1255608 | 1.235375227 |
| 58.7-51.9 | 54.78635173 | 1.254262131 |
| 51.9-45.5 | 48.17647142 | 1.274408627 |
| 45.5-40.2 | 42.44539909 | 1.293073999 |
| 40.2-36.1 | 37.876562 | 1.312338195 |
| 36.1-32.2 | 33.86330891 | 1.33343912 |
| 32.2-29.0 | 30.37788936 | 1.349636805 |

TABLE V-continued

Nitrogen Desorption Isotherm Data for CY15129

| Pore Diameter Range (Å) | Average Diameter (Å) | Cumulative Pore Volume (cm³/g) |
|---|---|---|
| 29.0-26.3 | 27.49677094 | 1.364920292 |
| 26.3-23.6 | 24.80122448 | 1.383211762 |
| 23.6-21.2 | 22.24825062 | 1.403332779 |
| 21.2-18.9 | 19.86056309 | 1.427226088 |
| 18.9-16.5 | 17.49279507 | 1.458083699 |

TABLE VI

Atomic Concentrations (in %) for CY15129

| Polymer | Condition | C | N | O | Na | S |
|---|---|---|---|---|---|---|
| CY15129 | Ground | 96.2 | 0.1 | 3.7 | 0.0 | 0.0 |

Example 3: Polymer Modification CY15154

20.05 g dried base polymer CY15077 was added to a 500 mL jacketed glass reactor, which was equipped with a Teflon coated agitator and RTD probe. Dried polymer was rewet into DI water making 100 mL slurry in reactor. 9.00 g zwitterionic neutral methacrylate monomer, [(2-methacryloyloxy)ethyl]-dimethyl-3-(sulfopropyl) ammonium hydroxide, and 1.1 g ammonium persulfate were dissolved in 100 mL DI water and the solution added to the reactor containing base polymer slurry. The mixture was heated to 75° C. and maintained at 75° C. for 24 hours with agitation at 100 RPM.

Work-up: reaction mixture was cooled to room temperature and washed with DI water until the pH of reaction supernatant was neutral. The result of the procedure was a poly(styrene-co-divinylbenzene) resin with sulfobetaine functionality.

Figure 2:
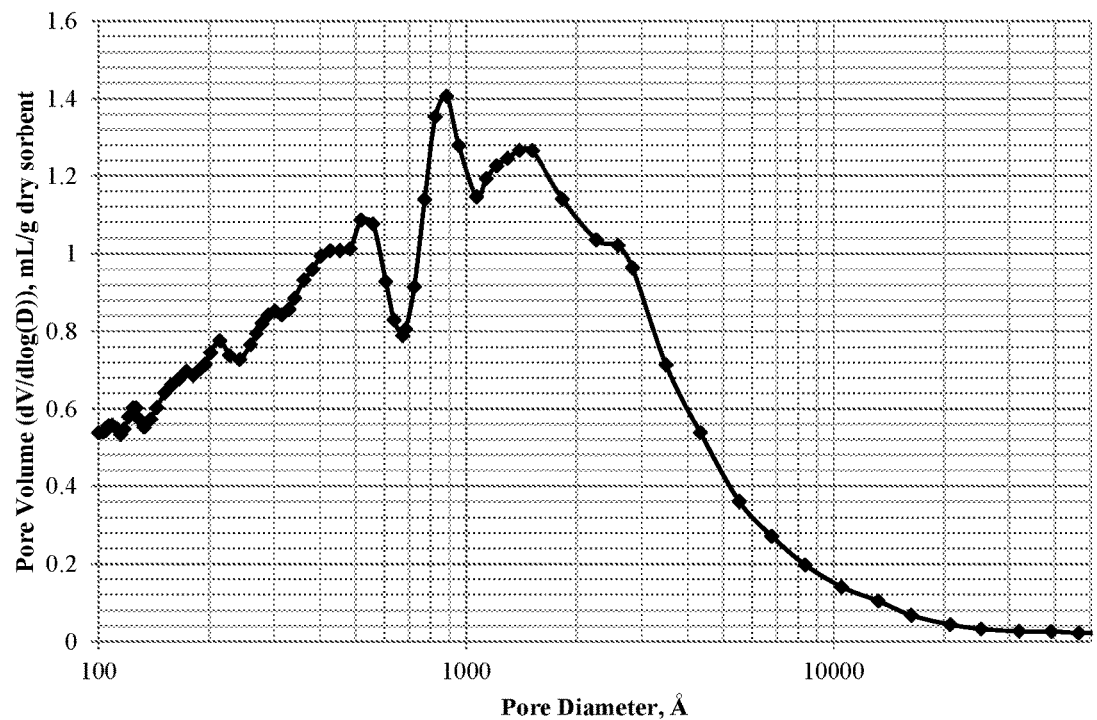

Cumulative pore volume data for polymer CY15154, measured by mercury intrusion porosimetry, is shown below in Table VII. Table VIII displays atomic concentrations for polymer CY15154, as measured by XPS. A log differential pore volume plot for polymer CY15154 presented in FIG. 2, below.

Thrombogenicity was measured by the uPTT assay in which materials were compared to the negative control (plasma alone), positive control (glass beads) and reference beads to determine the degree of contact activation activity. In the uPTT assay, the % change in clot formation over time as compared to the reference materials was determined, then grouped according to: <25% activators, 25-49% moderate activators, 50-74% mild activators, 75-100% minimal and >100% non-activators of the intrinsic coagulation pathway. Polymer CY15154, 89%, was a minimal activator.

TABLE VII

Mercury Intrusion Data for CY15154

| Pore size Diameter (Å) | Cumulative Intrusion (mL/g) |
|---|---|
| 226224.3281 | 3.71747E−30 |
| 213111.3594 | 0.001651293 |
| 201224.8906 | 0.002752155 |
| 172655.7656 | 0.005687786 |
| 139499.2344 | 0.00917385 |
| 113385.7891 | 0.012109481 |
| 90518.1875 | 0.014494682 |
| 78735.29688 | 0.015962498 |
| 72420.08594 | 0.017063361 |
| 60385.85547 | 0.019265084 |
| 46424.50391 | 0.021194145 |
| 39101.98438 | 0.023196908 |
| 31984.0625 | 0.0254653 |
| 25215.5918 | 0.028356753 |
| 20767.02734 | 0.031620611 |
| 16262.83203 | 0.037091091 |
| 13245.06152 | 0.044879291 |
| 10517.09473 | 0.0569603 |
| 8352.324219 | 0.073541678 |
| 6780.537109 | 0.094531983 |
| 5534.965332 | 0.122123614 |
| 4339.857422 | 0.168052331 |
| 3501.186768 | 0.227679923 |
| 2838.171631 | 0.301284552 |
| 2595.267822 | 0.342711538 |
| 2267.181396 | 0.401519477 |
| 1830.77832 | 0.502746403 |
| 1510.444214 | 0.602516055 |
| 1394.070435 | 0.649135411 |
| 1294.078247 | 0.688528717 |
| 1207.664307 | 0.725108385 |
| 1132.627563 | 0.760447145 |
| 1065.868652 | 0.791572869 |
| 953.7478638 | 0.843100905 |
| 883.8695679 | 0.884387076 |
| 823.3493652 | 0.94593215 |
| 770.980835 | 0.970002472 |
| 722.2579956 | 1.001678586 |
| 684.7388306 | 1.018621564 |
| 671.9746704 | 1.028800249 |
| 636.4578247 | 1.046198368 |
| 604.7978516 | 1.051783919 |
| 558.0610352 | 1.10215652 |
| 518.3203125 | 1.134908557 |
| 483.8748169 | 1.16506958 |
| 453.6493225 | 1.193175197 |
| 427.0003357 | 1.22020638 |
| 403.2171021 | 1.244618416 |
| 382.7931213 | 1.267649531 |
| 362.960968 | 1.290832281 |
| 342.2845154 | 1.310541511 |
| 330.1563721 | 1.326383829 |
| 315.566925 | 1.343571901 |
| 302.711731 | 1.357273817 |
| 290.2910767 | 1.371727705 |
| 279.088562 | 1.386254311 |
| 268.7399292 | 1.402165532 |
| 259.1445618 | 1.416057229 |
| 241.76651 | 1.434283853 |
| 226.8022308 | 1.453515768 |
| 213.4399872 | 1.475559831 |
| 201.5339813 | 1.494312882 |
| 195.092392 | 1.507889271 |
| 188.9113312 | 1.517046452 |
| 180.6271057 | 1.527027011 |
| 172.8740692 | 1.538419604 |
| 164.948822 | 1.556914806 |
| 157.7954102 | 1.56731689 |
| 151.1784973 | 1.587052464 |
| 143.9606934 | 1.589773178 |
| 138.4709473 | 1.602503777 |
| 132.876236 | 1.614367723 |
| 129.5559845 | 1.623571157 |
| 126.5602341 | 1.627325177 |
| 124.2691345 | 1.627749205 |
| 120.9029312 | 1.636968136 |
| 117.360611 | 1.64050591 |
| 114.767189 | 1.650183678 |
| 111.9378891 | 1.658891678 |
| 108.8768463 | 1.669423223 |
| 106.6498108 | 1.669423223 |

TABLE VII-continued

Mercury Intrusion Data for CY15154

| Pore size Diameter (Å) | Cumulative Intrusion (mL/g) |
|---|---|
| 104.528862 | 1.669845104 |
| 102.434761 | 1.670300245 |
| 100.163887 | 1.679309368 |
| 98.28566742 | 1.687124491 |
| 96.43279266 | 1.69373095 |
| 94.42179871 | 1.696792841 |
| 91.53875732 | 1.700315237 |
| 89.2629776 | 1.713412642 |
| 87.08113098 | 1.717851758 |
| 85.41996765 | 1.717851758 |
| 83.63195801 | 1.718092918 |
| 82.10193634 | 1.723257303 |
| 79.91257477 | 1.731604815 |
| 78.01113129 | 1.735616565 |
| 76.20046234 | 1.742268085 |
| 75.09152222 | 1.744680524 |
| 73.40940857 | 1.750109911 |
| 72.2360611 | 1.752892733 |
| 71.0995636 | 1.757597446 |
| 69.86175537 | 1.762209773 |
| 68.40699005 | 1.76675427 |
| 67.13555145 | 1.770863652 |
| 66.03234863 | 1.771475196 |
| 65.08116913 | 1.771476984 |
| 64.0411911 | 1.775840044 |
| 62.38346863 | 1.787451506 |
| 61.32735062 | 1.787451506 |
| 60.30354691 | 1.793258786 |
| 59.41280365 | 1.797853351 |
| 58.54663467 | 1.797853351 |
| 57.80006027 | 1.802747488 |
| 56.88902664 | 1.802747488 |
| 55.92008591 | 1.803194642 |
| 54.98501587 | 1.808090687 |

TABLE VIII

Atomic Concentrations (in %) for CY15154

| Polymer | Condition | C | N | O | Na | S |
|---|---|---|---|---|---|---|
| CY15154 | Ground | 93.9 | 0.7 | 4.8 | 0.1 | 0.6 |

Example 4: Polymer Modification CY16029

200 mL base polymer CY14175, wetted in DI water, was added to a 1000 mL jacketed glass reactor, which was equipped with a Teflon coated agitator and RTD probe. Excess water was removed from the reactor using a vacuum pump and filter tube. 500 mL 1.0M sodium hydroxide was added to the reactor. The mixture was heated to 50° C. and maintained at 50° C. for 24 hours with agitation at 100 RPM.

Work-up: reaction mixture was cooled to room temperature and washed with DI water until the pH of reaction supernatant was neutral. The result of the procedure was a poly(styrene-co-divinylbenzene) resin with diol functionality.

Example 5: Base Sorbent Synthesis CY15186

Reactor Setup: a 4-neck glass lid was affixed to a 1 L jacketed cylindrical glass reaction vessel using a stainless steel flange clamp and PFTE gasket. The lid was fitted with a PFTE stirrer bearing, RTD adapter, and water-cooled reflux condenser. A stainless steel stirring shaft having four 60° agitators was fit through the stirrer bearing and inserted into a digital overhead stirrer. An RTD was fit through the corresponding adapter, and connected to a PolyStat circulating heating and chilling unit. Compatible tubing was used to connect the inlet and outlet of the reaction vessel jacket to the appropriate ports on the PolyStat. The unused port in the lid was used for charging the reactor and was plugged at all other times.

Polymerization: Aqueous phase and organic phase compositions are shown below, in Table IX and Table X, respectively. Ultrapure water was added to an Erlenmeyer flask containing a PFTE coated magnetic stir bar. Poly(vinyl alcohol) (PVA), having a degree of hydrolysis of 85.0 to 89.0 mol percent and a viscosity of 23.0 to 27.0 cP in a 4% aqueous solution at 20° C., was dispersed into the water in the flask and heated to 80° C. on a hot plate with agitation. Circulation of heat transfer fluid from the PolyStat through the reaction vessel jacket was started, and fluid temperature heated to 60° C. Once PVA dissolved, the solution was charged to the reactor using a glass funnel. The digital overhead stirrer was powered on and the rpm set to a value to form appropriate droplet sizes upon organic phase addition. Temperature of the aqueous phase in the kettle was set to 70° C. The organic phase was prepared by adding benzoyl peroxide (BPO) to the divinylbenzene (DVB) and allyl glycidyl ether (AGE) in a 1 L Erlenmeyer flask and swirling until completely dissolved. 2,2,4-trimethylpentane and toluene were added to the flask, which was swirled to mix well. Once the temperature of the aqueous phase in the reactor reached 70° C., the organic phase was charged into the reactor using a narrow-necked glass funnel. Temperature of the reaction volume dropped upon the organic addition. A temperature program for the PolyStat was started, heating the reaction volume from 60 to 77° C. over 30 minutes, 77 to 80° C. over 30 minutes, holding the temperature at 80° C. for 960 minutes, and cooling to 20° C. over 60 minutes.

TABLE IX

Aqueous Phase Composition

| Reagent | Mass (g) |
|---|---|
| Ultrapure water | 501.505 |
| Poly(vinyl alcohol) (PVA) | 1.463 |
| Total | 502.968 |

TABLE X

Organic Phase Composition

| Reagent | Mass (g) |
|---|---|
| Divinylbenzene, 63% (DVB) | 149.518 |
| Allyl glycidyl ether (AGE) | 16.613 |
| 2,2,4-trimethylpentane (Isooctane) | 160.913 |
| Toluene | 74.134 |
| Benzoyl peroxide, 98% (BPO) | 1.246 |
| Total (excluding BPO) | 401.178 |

Work-up: reaction volume level in the reactor was marked. Overhead stirrer agitation was stopped, residual liquid siphoned out of the reactor, and the reactor filled to the mark with ultrapure water at room temperature. Overhead stirrer agitation was restarted and the slurry heated to 70° C. as quickly as possible. After 30 minutes, agitation was stopped and residual liquid siphoned out. Polymer beads were washed five times in this manner. During the final wash, the slurry temperature was cooled to room temperature. After the final water wash, polymer beads were washed with 99% isopropyl alcohol (IPA) in the same manner. 99% IPA was siphoned out and replaced with 70% IPA before transferring the slurry into a clean 2 L glass container. Unless noted otherwise, on an as-needed basis the polymer was steam stripped in a stainless steel tube for 8 hours, rewet in 70% IPA, transferred into DI water, sieved to obtain only the portion of beads having diameters between 300 and 600 m, and dried at 100° C. until no further weight loss on drying was observed.

Cumulative pore volume data for polymer CY15186, measured by mercury intrusion porosimetry, is shown below in Table XI.

TABLE XI

Mercury Intrusion Data for CY15186

| Pore size Diameter (Å) | Cumulative Intrusion (mL/g) |
|---|---|
| 226574.9688 | 4.16667E−30 |
| 213402.0781 | 0.00143953 |
| 201557.2031 | 0.002673413 |
| 172865.7813 | 0.005552473 |
| 139642.9063 | 0.008842826 |
| 113246.3672 | 0.01213318 |
| 90612.32813 | 0.016246123 |
| 78790.625 | 0.018096946 |
| 72482.59375 | 0.018919535 |
| 60373.96094 | 0.022004243 |
| 49330.66406 | 0.025782049 |
| 38828.21094 | 0.029563239 |
| 32281.45898 | 0.032648358 |
| 25408.87305 | 0.038482815 |
| 20836.85352 | 0.045313008 |
| 16161.98633 | 0.05680377 |
| 13229.80762 | 0.070135541 |
| 10529.51172 | 0.090406768 |
| 8364.625977 | 0.117706239 |
| 6782.583496 | 0.154166013 |
| 5537.970215 | 0.199266374 |
| 4336.817871 | 0.271772623 |
| 3498.797607 | 0.351178646 |
| 2839.945801 | 0.443094909 |
| 2594.289795 | 0.490598917 |
| 2268.72168 | 0.553719223 |
| 1830.803467 | 0.660846353 |
| 1510.359009 | 0.764178634 |
| 1394.668335 | 0.811257899 |
| 1294.491577 | 0.852448702 |
| 1208.005005 | 0.888583481 |
| 1131.924561 | 0.921772897 |
| 1066.473633 | 0.951730609 |
| 953.3641968 | 1.003630996 |
| 884.2562866 | 1.052415848 |
| 823.5280151 | 1.073814034 |
| 771.4370728 | 1.105411649 |
| 722.2237549 | 1.120140433 |
| 685.1390381 | 1.145742297 |
| 672.3484497 | 1.153626442 |
| 636.8387451 | 1.16934073 |
| 604.7866211 | 1.208441377 |
| 558.3435059 | 1.240501285 |
| 518.1854858 | 1.268068552 |
| 483.8361511 | 1.295331836 |
| 453.4187012 | 1.322064877 |
| 426.98349 | 1.346303344 |
| 403.1603394 | 1.367477417 |
| 382.764679 | 1.388786197 |
| 362.9465027 | 1.407936335 |
| 342.3362122 | 1.428686738 |
| 329.841217 | 1.442481041 |
| 315.7774048 | 1.456739783 |
| 302.3786621 | 1.468396068 |
| 290.1838379 | 1.481325388 |
| 279.0186768 | 1.494134068 |

TABLE XI-continued

Mercury Intrusion Data for CY15186

| Pore size Diameter (Å) | Cumulative Intrusion (mL/g) |
|---|---|
| 268.7069092 | 1.504692793 |
| 259.1578064 | 1.514950275 |
| 241.945694 | 1.532619953 |
| 226.7833557 | 1.550052524 |
| 213.419693 | 1.569337964 |
| 201.5121765 | 1.586070657 |
| 195.0518036 | 1.599830866 |
| 188.9384308 | 1.612305164 |
| 180.598114 | 1.617076278 |
| 172.8187256 | 1.627080917 |
| 164.9259338 | 1.637640119 |
| 157.7406464 | 1.652938724 |
| 151.21492 | 1.657568693 |
| 143.9346313 | 1.674796224 |
| 138.4336395 | 1.684575438 |
| 132.8709869 | 1.689449072 |
| 129.5866547 | 1.702379704 |
| 126.4979095 | 1.706433415 |
| 124.2752533 | 1.71120882 |
| 120.9342499 | 1.714904308 |
| 117.3752136 | 1.714904308 |
| 114.7828979 | 1.724609733 |
| 111.9247818 | 1.729753852 |
| 108.8955307 | 1.730157733 |
| 106.6599426 | 1.744294405 |
| 104.532135 | 1.746785283 |
| 102.4387283 | 1.75013876 |
| 100.1778946 | 1.75013876 |
| 98.2558136 | 1.750320315 |
| 96.43884277 | 1.753109574 |
| 94.43161011 | 1.756025434 |
| 91.53116608 | 1.759399176 |
| 89.26831055 | 1.777230859 |
| 87.07096863 | 1.777230859 |
| 85.41964722 | 1.780620933 |
| 83.62415314 | 1.780620933 |
| 82.10125732 | 1.785255194 |
| 79.90966034 | 1.788483143 |
| 78.01230621 | 1.788483143 |
| 76.20275879 | 1.788483143 |
| 75.0914917 | 1.788589239 |
| 73.41194916 | 1.788589239 |
| 72.23661041 | 1.788589239 |
| 71.10020447 | 1.789496899 |
| 69.86201477 | 1.800735831 |
| 68.40441895 | 1.80268836 |
| 67.13528442 | 1.80268836 |
| 66.03346252 | 1.810508251 |
| 65.08029175 | 1.81166029 |
| 64.04324341 | 1.822634697 |
| 62.3841629 | 1.825838447 |
| 61.32678223 | 1.828645229 |
| 60.30419159 | 1.830532074 |
| 59.41298676 | 1.830532074 |
| 58.54736328 | 1.830532074 |
| 57.79838181 | 1.830532074 |
| 56.88856888 | 1.830532074 |
| 55.92162704 | 1.83255136 |
| 54.98494339 | 1.832824707 |

Example 6: Polymer Modification CY16000

Ring Opening: 100 mL polymer CY15186, wetted in 70% IPA, was added to a 1 L jacketed glass reactor, which was equipped with a Teflon coated agitator and RTD probe. 300 mL 1M NaOH$_{(aq)}$ was added slowly. Reaction temperature was increased to 80° C. and held at 80° C. for 24 hours with agitation at 100 RPM.

Work-up: reaction was cooled to room temperature and washed with DI water until the pH of reaction supernatant was neutral. The result of the procedure was a poly(allyl glycidyl ether-co-divinylbenzene) resin functionalized with 1,2-diol groups.

Figure 3:
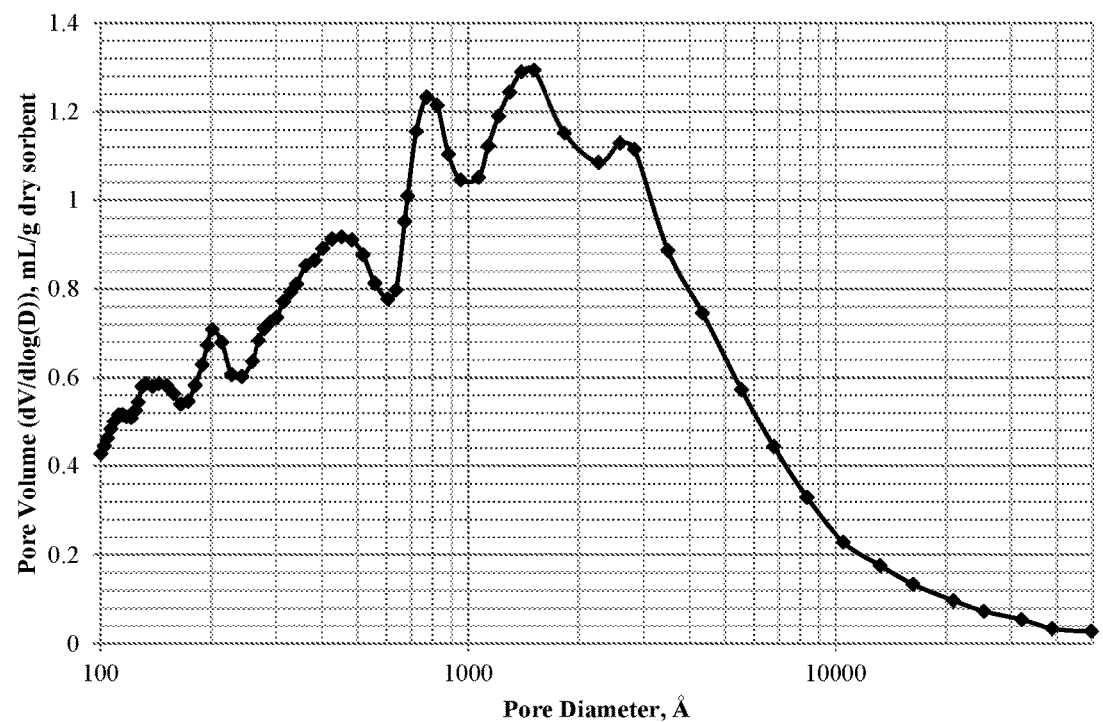

Cumulative pore volume data for polymer CY16000, measured by mercury intrusion porosimetry, is shown below in Table XII. Table XIII displays atomic concentrations for polymer CY16000, as measured by XPS. A log differential pore volume plot for polymer CY16000 is presented in FIG. 3, below.

Thrombogenicity was measured by the uPTT assay in which materials were compared to the negative control (plasma alone), positive control (glass beads) and reference beads to determine the degree of contact activation activity. In the uPTT assay, the % change in clot formation over time as compared to the reference materials was determined, then grouped according to: <25% activators, 25-49% moderate activators, 50-74% mild activators, 75-100% minimal and >100% non-activators of the intrinsic coagulation pathway. Polymer CY16000, 84%, was a minimal activator.

TABLE XII

Mercury Intrusion Data for CY16000

| Pore size Diameter (Å) | Cumulative Intrusion (mL/g) |
| --- | --- |
| 226237.4219 | 3.27869E−30 |
| 213116.6875 | 0.001780028 |
| 201256 | 0.002912772 |
| 172597.9375 | 0.005663724 |
| 139531.7344 | 0.008900138 |
| 113393.6016 | 0.011165627 |
| 90536.97656 | 0.013916579 |
| 78745.64844 | 0.016182069 |
| 72432.8125 | 0.017314814 |
| 60388.14063 | 0.020551227 |
| 49564.25391 | 0.023191452 |
| 38797.54688 | 0.025975971 |
| 32041.20898 | 0.029775988 |
| 25302.44141 | 0.036112998 |
| 20921.08984 | 0.043078985 |
| 16231.54297 | 0.055562966 |
| 13231.72168 | 0.069240041 |
| 10497.79492 | 0.089360692 |
| 8343.577148 | 0.116200015 |
| 6776.628418 | 0.151556209 |
| 5542.397949 | 0.195025146 |
| 4340.495117 | 0.265774131 |
| 3498.106201 | 0.341953665 |
| 2839.38623 | 0.430826575 |
| 2594.266846 | 0.478813648 |
| 2267.297852 | 0.540965915 |
| 1830.911011 | 0.644623816 |
| 1509.371948 | 0.745699465 |
| 1393.887939 | 0.794316649 |
| 1294.647949 | 0.83322984 |
| 1207.980835 | 0.869946182 |
| 1132.671631 | 0.903727651 |
| 1066.053711 | 0.932609558 |
| 953.1560059 | 0.978823841 |
| 883.3498535 | 1.016740084 |
| 823.050415 | 1.050323486 |
| 770.6383667 | 1.083085179 |
| 722.1539307 | 1.128799915 |
| 684.3758545 | 1.146574736 |
| 671.9072266 | 1.158596516 |
| 636.6184204 | 1.175545812 |
| 604.8302612 | 1.191316247 |
| 557.7293701 | 1.218484282 |
| 517.8145142 | 1.246015668 |
| 483.4432983 | 1.273180366 |
| 453.1549377 | 1.299499989 |
| 426.4946594 | 1.323516726 |
| 402.9095459 | 1.345747828 |
| 382.497406 | 1.366356015 |
| 362.7590942 | 1.386311769 |

TABLE XII-continued

Mercury Intrusion Data for CY16000

| Pore size Diameter (Å) | Cumulative Intrusion (mL/g) |
| --- | --- |
| 342.0608215 | 1.405492902 |
| 329.5023804 | 1.420231104 |
| 315.2943726 | 1.437522292 |
| 302.1650391 | 1.447153091 |
| 290.3215027 | 1.461028457 |
| 279.1251221 | 1.47798562 |
| 268.9230042 | 1.478424907 |
| 259.0871582 | 1.499376774 |
| 241.8872223 | 1.516182542 |
| 226.7401123 | 1.52628684 |
| 213.3443909 | 1.54687202 |
| 201.4691315 | 1.565247297 |
| 194.9713898 | 1.57622385 |
| 188.963913 | 1.586960673 |
| 180.6094666 | 1.597345948 |
| 172.8415527 | 1.605777144 |
| 164.9702148 | 1.615878105 |
| 157.8144836 | 1.62835598 |
| 151.1303864 | 1.637635469 |
| 143.9487305 | 1.651656628 |
| 138.4449463 | 1.661584258 |
| 132.878067 | 1.671312332 |
| 129.5904083 | 1.677082658 |
| 126.49086 | 1.684068799 |
| 124.2613449 | 1.68521893 |
| 120.9155121 | 1.696256876 |
| 117.3831711 | 1.70307827 |
| 114.7640991 | 1.709652185 |
| 111.9642258 | 1.709652185 |
| 108.8973465 | 1.710108638 |
| 106.6852188 | 1.719043851 |
| 104.4803925 | 1.726407647 |
| 102.4626007 | 1.730650187 |
| 100.1529846 | 1.738801718 |
| 98.26617432 | 1.742565274 |
| 96.43665314 | 1.744427681 |
| 94.44145203 | 1.744753599 |
| 91.53864288 | 1.750175834 |
| 89.26194763 | 1.750728965 |
| 87.08582306 | 1.755701542 |
| 85.41732788 | 1.764526129 |
| 83.63022614 | 1.765552759 |
| 82.10185242 | 1.769952536 |
| 79.9105835 | 1.773370266 |
| 78.01232147 | 1.782885909 |
| 76.19724274 | 1.791909099 |
| 75.08769226 | 1.792658687 |
| 73.40957642 | 1.796038389 |
| 72.23654175 | 1.796038389 |
| 71.09810638 | 1.796038389 |
| 69.86147308 | 1.796038389 |
| 68.40509033 | 1.796038389 |
| 67.13497925 | 1.796038389 |
| 66.03092957 | 1.797552824 |
| 65.08396149 | 1.802418113 |
| 64.04406738 | 1.802683711 |
| 62.38559723 | 1.813122511 |
| 61.32781601 | 1.813122511 |
| 60.30435562 | 1.821751833 |
| 59.41186142 | 1.823982239 |
| 58.54719925 | 1.823982239 |
| 57.79738235 | 1.825609565 |
| 56.8899765 | 1.825609565 |
| 55.91999054 | 1.834336996 |
| 54.98700714 | 1.834405422 |

TABLE XIII

Atomic Concentrations (in %) for CY16000

| Polymer | Condition | C | N | O | Na | S |
|---|---|---|---|---|---|---|
| CY16000 | Ground | 98.8 | 0.0 | 1.2 | 0.0 | 0.0 |

Example 7: Base Sorbent Synthesis CY16207

Reactor Setup: a 4-neck glass lid was affixed to a 3 L jacketed cylindrical glass reaction vessel using a stainless steel flange clamp and PFTE gasket. The lid was fitted with a PFTE stirrer bearing, RTD adapter, and water-cooled reflux condenser. A stainless steel stirring shaft having five 60° agitators was fit through the stirrer bearing and inserted into a digital overhead stirrer. An RTD was fit through the corresponding adapter, and connected to a PolyStat circulating heating and chilling unit. Compatible tubing was used to connect the inlet and outlet of the reaction vessel jacket to the appropriate ports on the PolyStat. The unused port in the lid was used for charging the reactor and was plugged at all other times.

Polymerization: Aqueous phase and organic phase compositions are shown below, in Table XIV and Table XV, respectively. Ultrapure water was split into approximately equal parts in two separate Erlenmeyer flasks, each containing a PFTE coated magnetic stir bar. Poly(vinyl alcohol) (PVA), having a degree of hydrolysis of 85.0 to 89.0 mol percent and a viscosity of 23.0 to 27.0 cP in a 4% aqueous solution at 20° C., was dispersed into the water in the first flask and heated to 80° C. on a hot plate with agitation. Salts (see Table 1, MSP, DSP, TSP and Sodium nitrite) were dispersed into the water in the second flask and heated to 80° C. on a hot plate with agitation. Circulation of heat transfer fluid from the PolyStat through the reaction vessel jacket was started, and fluid temperature heated to 60° C. Once PVA and salts dissolved, both solutions were charged to the reactor, one at a time, using a glass funnel. The digital overhead stirrer was powered on and the rpm set to a value to form appropriate droplet sizes upon organic phase addition. Temperature of the aqueous phase in the kettle was set to 60° C. The organic phase was prepared by adding benzoyl peroxide (BPO) to the divinylbenzene (DVB) and vinyl acetate (VA) in a 2 L Erlenmeyer flask and swirling until completely dissolved. 2,2,4-trimethylpentane and toluene were added to the flask, which was swirled to mix well. Once the temperature of the aqueous phase in the reactor reached 60° C., the organic phase was charged into the reactor using a narrow-necked glass funnel. Temperature of the reaction volume dropped upon the organic addition. A temperature program for the PolyStat was started, heating the reaction volume from 50 to 67° C. over 30 minutes, 67 to 70° C. over 30 minutes, holding the temperature at 70° C. for 960 minutes, and cooling to 20° C. over 60 minutes.

TABLE XIV

Aqueous Phase Composition

| Reagent | Mass (g) |
|---|---|
| Ultrapure water | 1504.514 |
| Poly(vinyl alcohol) (PVA) | 4.388 |
| Monosodium phosphate (MSP) | 4.639 |
| Disodium phosphate (DSP) | 15.358 |
| Trisodium phosphate (TSP) | 9.529 |
| Sodium nitrite | 0.050 |
| Total | 1533.899 |

TABLE XV

Organic Phase Composition

| Reagent | Mass (g) |
|---|---|
| Divinylbenzene, 63% (DVB) | 184.489 |
| Vinyl acetate (VA) | 276.734 |
| 2,2,4-trimethylpentane (Isooctane) | 519.415 |
| Toluene | 217.344 |
| Benzoyl peroxide, 98% (BPO) | 7.060 |
| Total (excluding BPO) | 1197.981 |

Work-up: reaction volume level in the reactor was marked. Overhead stirrer agitation was stopped, residual liquid siphoned out of the reactor, and the reactor filled to the mark with ultrapure water at room temperature. Overhead stirrer agitation was restarted and the slurry heated to 70° C. as quickly as possible. After 30 minutes, agitation was stopped and residual liquid siphoned out. Polymer beads were washed five times in this manner. During the final wash, the slurry temperature was cooled to room temperature. After the final water wash, polymer beads were washed with 99% isopropyl alcohol (IPA) in the same manner. 99% IPA was siphoned out and replaced with 70% IPA before transferring the slurry into a clean 4 L glass container. Unless noted otherwise, on an as-needed basis the polymer was steam stripped in a stainless steel tube for 8 hours, rewet in 70% IPA, transferred into DI water, sieved to obtain only the portion of beads having diameters between 300 and 600 m, then stored in 70% IPA.

Example 8: Polymer Modification CY16083

Ring Opening: 100 mL polymer CY16207, wetted in 70% IPA, was added to a 1 L jacketed glass reactor, which was equipped with a Teflon™ coated agitator and RTD probe. 300 mL 1M $NaOH_{(aq)}$ was added slowly. Reaction temperature was increased to 50° C. and held at 50° C. for 24 hours with agitation at 100 RPM.

Work-up: reaction was cooled to room temperature and washed with DI water until the pH of reaction supernatant was neutral. The result of the procedure was a poly(vinyl acetate-co-divinylbenzene) resin functionalized with diol groups.

Figure 4:
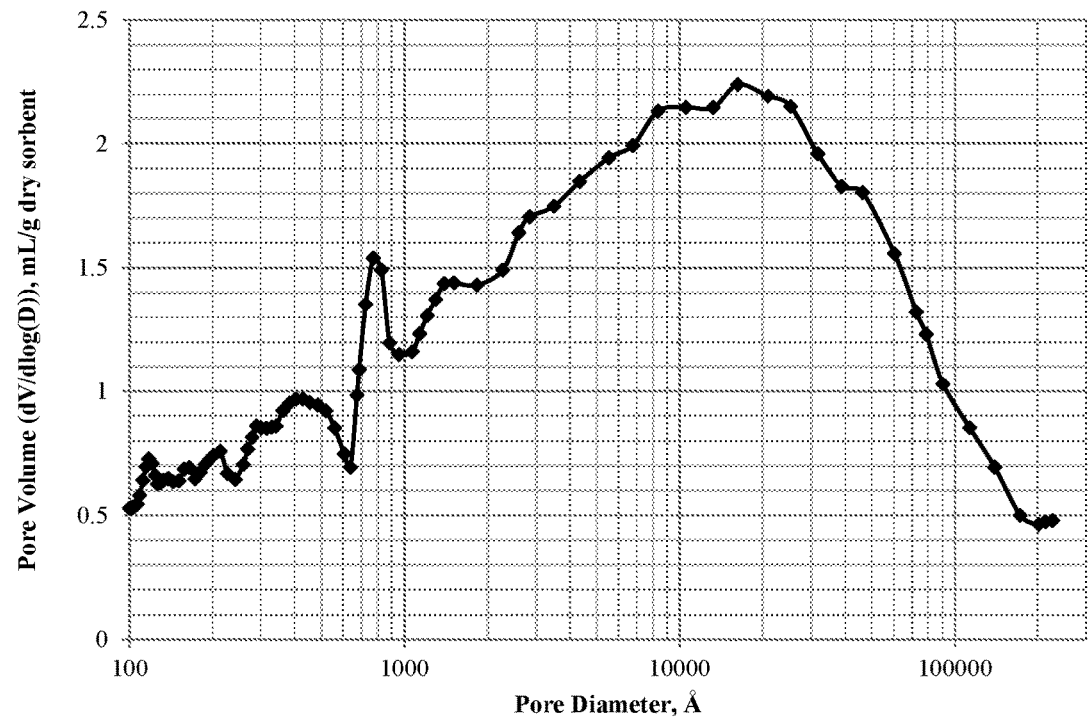

Cumulative pore volume data for polymer CY16083, measured by mercury intrusion porosimetry, is shown below in Table XVI. A log differential pore volume plot for polymer CY16083 is presented in FIG. 4, below.

TABLE XVI

Mercury Intrusion Data for CY16083

| Pore size Diameter (Å) | Cumulative Intrusion (mL/g) |
|---|---|
| 226391.9063 | 4.78469E−30 |
| 213308.9531 | 0.012976322 |
| 201386.2656 | 0.02406518 |
| 172686.375 | 0.054736488 |
| 139546.625 | 0.109237045 |
| 113150.9688 | 0.18072477 |
| 90562.88281 | 0.269671559 |
| 78762.24219 | 0.337856233 |
| 72451.34375 | 0.385278791 |
| 60349.18359 | 0.496875197 |
| 46204.09375 | 0.697754502 |
| 38763.8125 | 0.836230755 |
| 31643.42969 | 1.000192761 |
| 25230.56055 | 1.205377698 |

TABLE XVI-continued

Mercury Intrusion Data for CY16083

| Pore size Diameter (Å) | Cumulative Intrusion (mL/g) |
| --- | --- |
| 20887.55078 | 1.38317883 |
| 16239.9668 | 1.625140905 |
| 13230.17285 | 1.826209903 |
| 10526.66992 | 2.024656534 |
| 8343.935547 | 2.255314827 |
| 6768.749023 | 2.437402248 |
| 5536.999023 | 2.610224247 |
| 4339.233398 | 2.809215069 |
| 3496.317871 | 2.979628563 |
| 2839.894531 | 3.132294893 |
| 2594.126465 | 3.201504469 |
| 2269.560547 | 3.289848328 |
| 1830.92041 | 3.426440239 |
| 1510.197266 | 3.543637514 |
| 1394.337891 | 3.59655261 |
| 1294.366821 | 3.639976263 |
| 1208.313232 | 3.682707548 |
| 1132.399414 | 3.715785503 |
| 1065.535278 | 3.749961376 |
| 953.255188 | 3.801620483 |
| 883.243103 | 3.842084646 |
| 823.732666 | 3.878456354 |
| 770.7653809 | 3.914454937 |
| 722.7271118 | 3.989947796 |
| 684.5341187 | 3.999229193 |
| 672.2802734 | 4.007525921 |
| 636.6481934 | 4.021618843 |
| 604.5131836 | 4.041242599 |
| 558.1253662 | 4.064183712 |
| 518.5241089 | 4.095198154 |
| 483.8094177 | 4.125536919 |
| 453.6139832 | 4.149884224 |
| 427.0258789 | 4.17394495 |
| 403.3308411 | 4.201014519 |
| 382.3586426 | 4.224377632 |
| 362.4940186 | 4.242950439 |
| 342.3064575 | 4.266281605 |
| 329.9550171 | 4.28075552 |
| 315.6726379 | 4.299653053 |
| 302.4161987 | 4.306960106 |
| 290.1585083 | 4.327187061 |
| 279.201416 | 4.34189415 |
| 268.7153015 | 4.355234623 |
| 259.0892944 | 4.374240398 |
| 241.8599091 | 4.383106709 |
| 226.7653198 | 4.401435852 |
| 213.347641 | 4.423255444 |
| 201.5104675 | 4.442746162 |
| 194.9966431 | 4.454417229 |
| 188.9203796 | 4.464861393 |
| 180.6326904 | 4.472812653 |
| 172.8411407 | 4.489228249 |
| 164.9724884 | 4.502909184 |
| 157.8284607 | 4.51300478 |
| 151.176178 | 4.524533749 |
| 143.9182281 | 4.549272537 |
| 138.4604645 | 4.55087471 |
| 132.8447571 | 4.55614233 |
| 129.5848236 | 4.571050644 |
| 126.493721 | 4.576627254 |
| 124.2370682 | 4.585023403 |
| 120.9169006 | 4.589932919 |
| 117.3489761 | 4.599758148 |
| 114.7642288 | 4.605149269 |
| 111.946228 | 4.6123209 |
| 108.9087601 | 4.619316101 |
| 106.6530533 | 4.630918026 |
| 104.5154953 | 4.637215614 |
| 102.4490051 | 4.64176178 |
| 100.1706924 | 4.642546177 |
| 98.26054382 | 4.642546177 |
| 96.43994141 | 4.642546177 |
| 94.42762756 | 4.646022797 |
| 91.53787994 | 4.659168243 |
| 89.26939392 | 4.670140743 |
| 87.08105469 | 4.674285412 |
| 85.43276978 | 4.682890892 |
| 83.63574219 | 4.683265686 |
| 82.1003418 | 4.688156128 |
| 79.91436768 | 4.694897175 |
| 78.01213074 | 4.699482918 |
| 76.19928741 | 4.706587791 |
| 75.09382629 | 4.709022045 |
| 73.41336823 | 4.713496685 |
| 72.2383728 | 4.720668793 |
| 71.10043335 | 4.723160267 |
| 69.86404419 | 4.731044769 |
| 68.40866852 | 4.73837328 |
| 67.13607788 | 4.73837328 |
| 66.03302765 | 4.73837328 |
| 65.08182526 | 4.738733292 |
| 64.04320526 | 4.744318962 |
| 62.38569641 | 4.75237608 |
| 61.32912827 | 4.755572319 |
| 60.30617142 | 4.758491516 |
| 59.41395187 | 4.765036583 |
| 58.5463829 | 4.765704632 |
| 57.79882813 | 4.769648552 |
| 56.88949585 | 4.773656368 |
| 55.92075729 | 4.779618263 |
| 54.98794556 | 4.780755997 |

Example 9: Pore Structure Summary and Classification

Pore structure, including pore size, pore size distribution, and surface properties, is very important to the adsorption characteristics of porous material. IUPAC has classified pores into micropores, mesopores, and macropores; terms which are widely used in adsorption, catalysis, and other areas.

Micropores have widths smaller than 2 nm (<20 Å).

Mesopores have widths between 2 and 50 nm (20 Å ~500 Å).

Macropores have widths larger than 50 nm (>500 Å).

Under IUPAC's definition, pore size (or pore diameter) is the distance between two opposite walls of the pore and therefore refer to the diameter of cylindrical pores, or the width of slit-shaped pores. In addition to the IUPAC classification, the term transport pores (with pore diameter greater than 250 Å) has been used in the area of activated carbon adsorption. For the purpose of illustration in this application, the term "large transport pores" refers to pores with a diameter greater than 2,000 Å, as a subgroup of macropores; the term "capacity pores" refers to pores with diameter greater than 100 Å, and are capable of adsorbing small and midsize biomolecules and proteins (to 50 kDa); and the term "effective pores" refers to pores with a diameter within the range of 100~250 Å. which is a subgroup of mesopores and has shown to be the most effective pores for small and midsize protein adsorption.

While mesopores are useful adsorption sites, the macropores provide a transfer path for adsorbate to reach the inner adsorption sites. The large transport pores provide a much more effective transfer path that is particularly important for large molecules, such as large proteins, endotoxins, and other large toxin molecules. This invention discloses the technique of producing a wide pore size distribution, including large transport pores, conventional macropores, mesopores, and micropores, to complement special needs in adsorption applications. Table XVII summarizes the pore size distribution of polymer examples disclosed in this application, including IUPAC classifications and size fractions important to protein and biomolecule adsorption.

cal concentrations and recirculated through a 20 mL polymer-filled device at a flow rate of 140 mL/min for five hours. Proteins and initial concentrations were: IL-6 3000 pg/mL

TABLE XVII

Pore Data Summary

| | Polymer ID | | | | | | |
|---|---|---|---|---|---|---|---|
| | CY14175 | CY15129 | CY15077 | CY15154 | CY15186 | CY16000 | CY16083 |
| Porosimetly Method | Nitrogen Desorption | Nitrogen Desorption | Mercury Intrusion | Mercury Intrusion | Mercury Intrusion | Mercury Intrusion | Mercury Intrusion |
| Total Pore Volume, cc/g; Dp > 16 Å | 1.9778 | 1.4581 | 2.3034 | 1.8081 | 1.8328 | 1.8344 | 4.7808 |
| Capacity Pore Volume, cc/g; Dp > 100 Å | 1.5433 | 1.1418 | 2.1830 | 1.6800 | 1.7502 | 1.7391 | 4.6425 |
| Effective Pore Volume, cc/g; Dp, 100 Å→250 Å | 0.3500 | 0.2550 | 0.2369 | 0.2543 | 0.2258 | 0.2309 | 0.2683 |
| Transport Pore Volume of Dp > 250 Å, cc/g | 1.1933 | 0.8868 | 1.9461 | 1.4256 | 1.5244 | 1.5083 | 4.3742 |
| Large Transport Pore Volume, cc/g; Dp > 2,000 Å | ~0 | 0 | 1.0108 | 0.4635 | 0.6195 | 0.6045 | 3.2898 |
| Macropore Volume, cc/g; Dp > 500 Å | 0.6026 | 0.3655 | 1.6945 | 1.1510 | 1.2825 | 1.2601 | 4.0952 |
| Mesopore Volume, cc/g; Dp: 20→500 Å | 1.3125 | 1.0503 | 0.6089 | 0.6571 | 0.5503 | 0.5743 | 0.6856 |
| Micropore Volume, cc/g; Dp < 20 Å | 0.0627 | 0.0423 | 0.0000 | 0.0000 | 0.0000 | 0.0000 | 0.0000 |
| Capacity Pore Volume, % of total pore vol | 78% | 78% | 95% | 93% | 95% | 95% | 97% |
| Effective Pore Volume, % of total pore vol | 18% | 17% | 10% | 14% | 12% | 13% | 6% |
| Transport Pore Volume, % of total pore vol | 60% | 61% | 84% | 79% | 83% | 82% | 92% |
| Large Transport Pore Volume, % of total pore vol | 0% | 0% | 44% | 26% | 34% | 33% | 69% |
| Macropore Volume, % of total pore vol | 30% | 25% | 74% | 64% | 70% | 69% | 86% |
| Mesopore Volume, % of total pore vol | 66% | 92% | 28% | 39% | 31% | 33% | 14% |
| Micropore Volume, % of total pore vol | 3.2% | 4% | 0% | 0% | 0% | 0% | 0% |

Dp = Pore Diameter
vol = volume
>: greater
<: smaller
~: approximately
→: to (for range)

Figure 5:
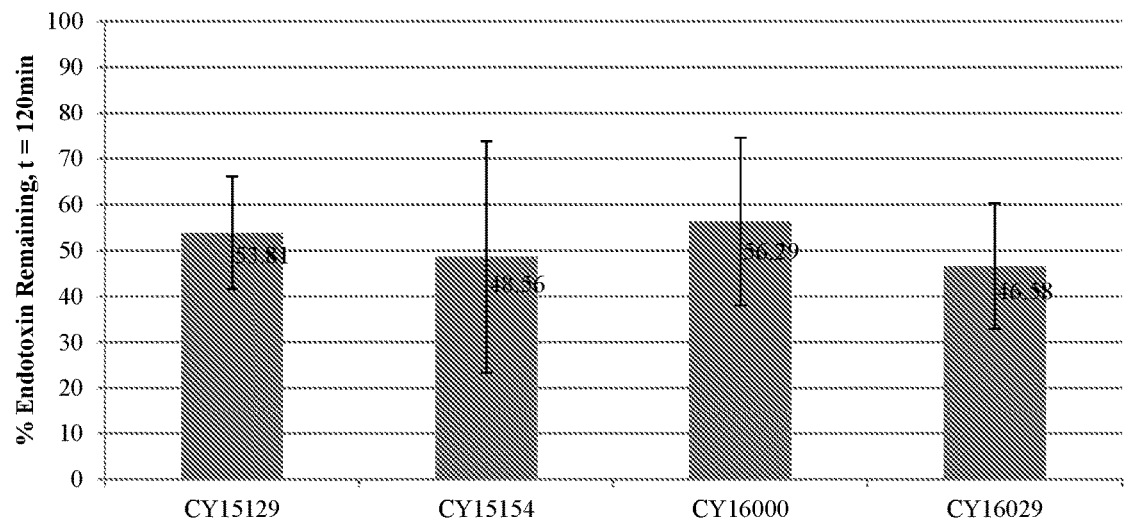
FIG. 5 presents endotoxin removal data from a dynamic model, in human plasma, expressed as a percentage determined by the amount of endotoxin remaining after 120 minutes compared to the pre-circulation concentration for modified polymers CY15129, CY15154, CY16000 and CY16029.
Figure 6:
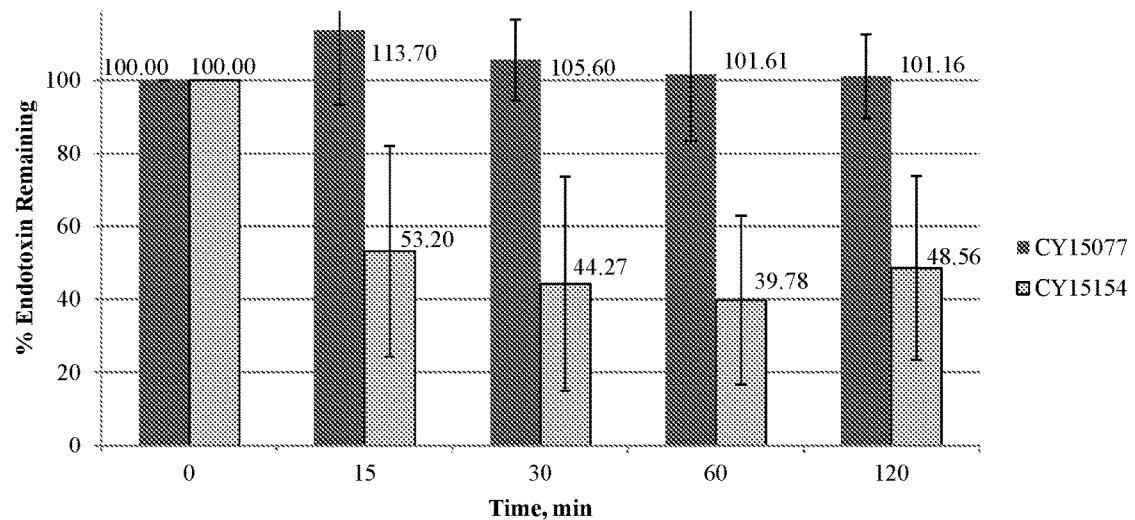
FIG. 6 shows endotoxin removal data from a dynamic model, in human plasma, expressed as a percentage determined by the amount of endotoxin remaining after 120 minutes compared to the pre-circulation concentration for polymer CY15154 and its non-modified precursor CY15077.

Example 10: Endotoxin Removal from Plasma in a Recirculation Model 20 mL of heat-inactivated human citrated plasma was spiked with 3 EU/ml endotoxin purchased from Associates of Cape Cod, East Falmouth, Mass., and then spiked into plasma reservoir. Plasma with endotoxin was mixed on stir plate for 15 minutes and recirculated through the 1.5 mL polymer column at a flow rate of 2.5 mL/min. Samples were collected from the reservoir using sterile pipette tips and diluted 1:20 in endotoxin-free water. All diluted samples were tested in the Pierce LAL Endotoxin Assay from Life Technologies, Corp., Grand Island, N.Y. Data for endotoxin removal from plasma in dynamic recirculation model, using modified polymers CY15129, CY15154, CY16000, and CY16029 is shown below, in FIG. 5. FIG. 6 presents endotoxin removal data for polymer CY15154 and its non-modified precursor polymer CY15077.

Example 11: Cytokine Removal from Whole Bovine Blood in a Recirculation Model

Figure 7:
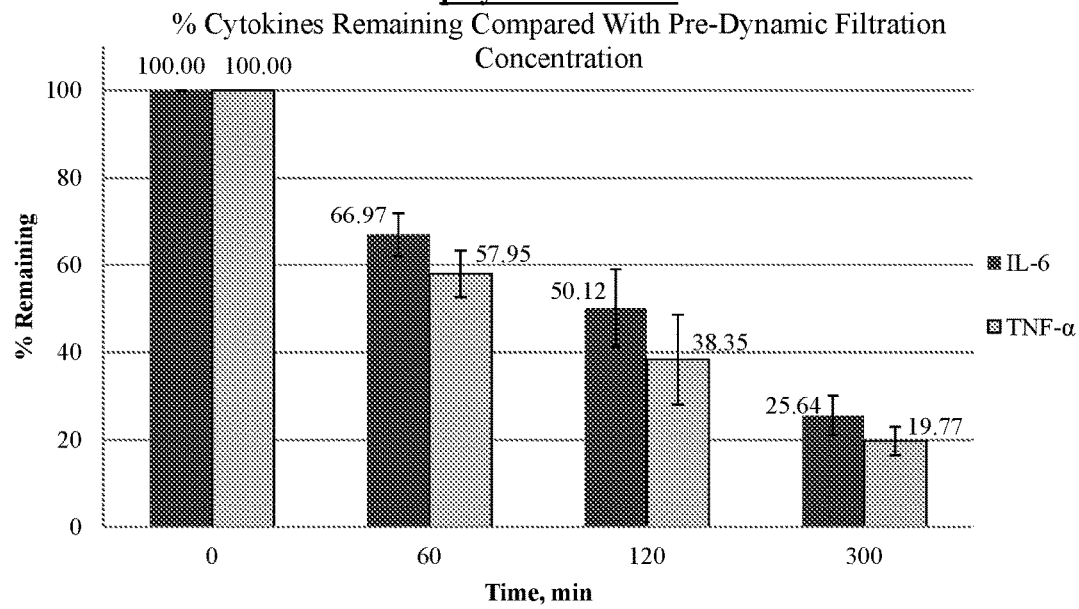
FIG. 7 displays cytokine removal data from a dynamic model, in whole blood, expressed as a percentage determined by the amount of cytokines remaining at specified time points compared to the pre-circulation concentration.

Purified proteins were added to 300 mL 3.8% citrated whole bovine blood (Lampire Biologicals) at expected cliniand TNF-α at 800 pg/mL. Plasma was analyzed by enzyme-linked immunosorbent assay (ELISA) following manufacturer instructions (R&D Systems). Data for cytokine removal from whole blood using polymer CY15129 in a dynamic recirculation model is shown below, in FIG. 7.

What is claimed:
1. A method of adsorbing endotoxins comprising contacting physiologic fluid with a polymer system comprising either polyol or zwitterionic functionality; said polymer system has the form of a solid support having a polymer coating comprising poly(diethylaminoethyl methacrylate), poly(dimethylaminoethyl methacrylate), poly(hydroxyethyl acrylate), poly(hydroxyethyl methacrylate), poly(hydroxypropyl acrylate), poly (hydroxypropyl methacrylate), poly (N-vinylpyrrolidone), poly(vinyl alcohol), salts of poly (acrylic acid), salts of poly(methacrylic) acid, or mixtures thereof.
2. The method of claim 1, wherein the polymer system is also capable of adsorbing a broad range of toxins and inflammatory mediators.
3. The method of claim 2 wherein the said toxins and inflammatory mediators have a molecular weight of from less than 0.5 kDa to 1,000 kDa.

4. The method of claim 2 wherein the said toxins and inflammatory mediators have a molecular weight of from less than 0.5 kDa to 60 kDa.

5. The method of claim 2 wherein the toxins and inflammatory mediators comprise one or more of cytokines, pathogen-associated molecular pattern molecules (PAMPs), damage-associated molecular pattern molecules (DAMPs), superantigens, monokines, chemokines, interferons, proteases, enzymes, peptides including bradykinin, soluble CD40 ligand, bioactive lipids, oxidized lipids, cell-free hemoglobin, cell-free myoglobin, growth factors, glycoproteins, prions, toxins, bacterial and viral toxins, drugs, vasoactive substances, foreign antigens, and antibodies.

6. The method of claim 1 wherein the polymer system is also capable of adsorbing one or more of gram-negative bacteria, gram-negative bacteria fragments, and gram-negative bacterial components.

7. The method of claim 1 wherein the polymer system is also capable of adsorbing one or more of gram-positive bacteria, gram-positive bacteria fragments, and gram-positive bacterial components.

8. The method of claim 1 wherein the solid support is selected from beads, fibers, monolithic columns, film, membranes, or semi-permeable membranes.

9. The method of claim 1 wherein the polymer system comprises a plurality of pores and a total volume of pore sizes in the range of from 10 Å to 40,000 Å greater than 0.1 cc/g and less than 5.0 cc/g dry polymer.

10. The method of claim 1, wherein the polymer system is nonporous.

11. The method of claim 1 wherein the polymer system further comprises a hypercrosslinked polymer.

12. The method of claim 1 wherein the polymer system further comprises either (i) heparin or (ii) a heparin mimicking polymer.

13. The method of claim 1, comprising passing the physiologic fluid one or more times through an extracorporeal circuit comprising a device comprising the polymer system.

14. The method of claim 1 wherein the polymer system further comprises a macroreticular porous polymer.

* * * * *